US009127324B2

(12) United States Patent
Shin et al.

(10) Patent No.: US 9,127,324 B2
(45) Date of Patent: Sep. 8, 2015

(54) O-PHOSPHOSERINE SULFHYDRYLASE MUTANTS AND METHOD FOR PRODUCTION OF CYSTEINE USING THE SAME

(75) Inventors: Soo An Shin, Seoul (KR); Jin Sook Chang, Seoul (KR); Hye Won Um, Suwon-si (KR); Jae Hyun Jo, Seoul (KR); Byeong Cheol Song, Uiwang-si (KR); Kyoung Min Lee, Daejeon (KR)

(73) Assignee: CJ Cheildjedang Corporation (KR)

( * ) Notice: Subject to any disclaimer, the term of this patent is extended or adjusted under 35 U.S.C. 154(b) by 0 days.

(21) Appl. No.: 13/278,100

(22) Filed: Oct. 20, 2011

(65) Prior Publication Data

US 2012/0190080 A1 Jul. 26, 2012

(30) Foreign Application Priority Data

Oct. 20, 2010 (KR) ........................ 10-2010-0102665

(51) Int. Cl.
*C12N 9/10* (2006.01)
*C12P 13/12* (2006.01)

(52) U.S. Cl.
CPC ....... *C12Y 205/01065* (2013.01); *C12N 9/1085* (2013.01); *C12P 13/12* (2013.01)

(58) Field of Classification Search
CPC ........ C12N 9/1085; C12N 9/16; C12P 13/12; C12P 13/06; C12Y 205/01065; C12Y 205/01113
USPC ............................ 435/193, 69.1, 15; 530/350
See application file for complete search history.

(56) References Cited

U.S. PATENT DOCUMENTS

2005/0255568 A1 11/2005 Bailey et al.

FOREIGN PATENT DOCUMENTS

EP 0 885 962 B1 4/2005
JP 2009501512 A 1/2009

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Fleischmann et al., GenBank accession No. ABK70074, Mar. 9, 2010.*
NCBI Database: Accession YP 889160, cysteine synthase B [*Mycobacterium smegmatis* str. MC2 155].
Agren et al., "The C-terminal of CysM from *Mycobacterium tuberculosis* protects the aminoacrylate intermediate and is involved in sulfur donor selectivity," FEBS Letters 583: 330-336, 2009.
Burns et al., "Reconstitution of a New Cysteine Biosynthetic Pathway in *Mycobacterium tuberculosis*," J. Am. Chem. Soc., 127: 11602-11603, 2005.
Mino et al., "A novel O-phospho-L-serine sulfydrylation reaction catalyzed by O-acetylserine sulfydrylase from *Aeropyrum pernix* K1," FEBS Letters 551: 133-138, 2003.
Ryu et al., "Continuous L-cysteine production using immobilized cell reactors and product extractors," Process Biochemistry 32(3): 201-209, 1997.
Wada et al., "Metabolic pathways and biotechnological production of L-cysteine," Appl. Microbiol. Biotechnol. 73: 48-54, 2006.
Westrop et al., "Cysteine Biosynthesis in *Trichomonas vaginalis* Involves Cysteine Synthase Utilizing O- Phosphoserine," The Journal of Biological Chemistry 281(35): 25062-25075, 2006.

* cited by examiner

*Primary Examiner* — Delia Ramirez
(74) *Attorney, Agent, or Firm* — Cooley LLP

(57) ABSTRACT

Disclosed is an O-phosphoserine sulfhydrylase (OPSS) mutant which has a *Mycobacterium smegmatis*-derived amino acid sequence corresponding to that of SEQ ID NO: 1 which is devoid of three to seven C-terminal amino acid residues. Also, a nucleic acid molecule encoding the OPSS mutant, an expression vector carrying the nucleic acid molecule, and a transformant transformed with the expression vector are disclosed. In addition, a method is provided for producing cysteine in which O-phospho-L-serine (OPS) is reacted with a sulfide in the presence of the OPSS mutant. The OPSS mutant has improved enzymatic activity and can be applied to the environmentally friendly production of L-cysteine through a simple enzymatic conversion reaction.

11 Claims, 6 Drawing Sheets

SEQUENCE LISTING

```
<160> NUMBER OF SEQ ID NOS: 26

<210> SEQ ID NO 1
<211> LENGTH: 323
<212> TYPE: PRT
<213> ORGANISM: Artificial Sequence
<220> FEATURE:
<223> OTHER INFORMATION: Msm-OPSS from Mycobacterium smegmatics str.
      MC2 155

<400> SEQUENCE: 1

Met Thr Arg Tyr Asp Ser Leu Leu Gln Ala Leu Gly Asn Thr Pro Leu
1               5                   10                  15

Val Gly Leu Gln Asn Leu Ser Pro Arg Trp Asp Asp Glu Asp Gly Lys
            20                  25                  30

Pro His Val Arg Leu Trp Ala Lys Leu Glu Asp Arg Asn Pro Thr Gly
        35                  40                  45

Ser Ile Lys Asp Arg Pro Ala Leu Arg Met Ile Glu Gln Ala Glu Arg
    50                  55                  60

Asp Gly Leu Leu Gln Pro Gly Ala Thr Ile Leu Glu Pro Thr Ser Gly
65                  70                  75                  80

Asn Thr Gly Ile Ser Leu Ala Met Ala Ala Leu Leu Lys Gly Tyr Asn
                85                  90                  95

Met Ile Cys Val Met Pro Glu Asn Thr Ser Ile Glu Arg Arg Gln Ile
            100                 105                 110

Leu Glu Leu Tyr Gly Ala Arg Ile Ile Phe Ser Pro Ala Glu Gly Gly
        115                 120                 125

Ser Asn Thr Ala Val Ala Thr Ala Lys Glu Leu Ala Ala Gln Asn Pro
```

-continued

```
    130                 135                 140

Ser Trp Val Met Leu Tyr Gln Tyr Gly Asn Pro Ala Asn Ser Asp Ala
145                 150                 155                 160

His Tyr Phe Gly Thr Gly Pro Glu Leu Leu Ala Asp Leu Pro Glu Ile
                165                 170                 175

Thr His Phe Val Ala Gly Leu Gly Thr Thr Gly Thr Leu Met Gly Thr
            180                 185                 190

Gly Arg Phe Leu Arg Glu His Val Pro Gly Val Gln Ile Val Ala Ala
        195                 200                 205

Glu Pro Arg Tyr Gly Glu Gly Val Tyr Ala Leu Arg Asn Ile Asp Glu
    210                 215                 220

Gly Phe Ile Pro Glu Leu Tyr Asp Ala Asp Val Leu Thr Thr Arg Phe
225                 230                 235                 240

Ser Val Gly Ser Phe Asp Ala Val Arg Arg Thr Arg Glu Leu Val Thr
                245                 250                 255

Arg Glu Gly Ile Phe Ala Gly Ile Ser Thr Gly Ala Val Leu His Ala
            260                 265                 270

Ala Leu Gly Met Ala Ala Lys Ala Val Lys Ala Gly Glu Arg Ala Asp
        275                 280                 285

Ile Ala Phe Val Val Ala Asp Ala Gly Trp Lys Tyr Leu Ser Thr Gly
    290                 295                 300

Ala Tyr Ala Gly Ser Leu Asp Asp Ala Glu Asp Ala Leu Glu Gly Gln
305                 310                 315                 320

Leu Trp Ala


<210> SEQ ID NO 2
<211> LENGTH: 318
<212> TYPE: PRT
<213> ORGANISM: Artificial Sequence
<220> FEATURE:
<223> OTHER INFORMATION: Msm-T from Mycobacterium smegmatics str. MC2
      155

<400> SEQUENCE: 2

Met Thr Arg Tyr Asp Ser Leu Leu Gln Ala Leu Gly Asn Thr Pro Leu
1               5                   10                  15

Val Gly Leu Gln Asn Leu Ser Pro Arg Trp Asp Asp Glu Asp Gly Lys
            20                  25                  30

Pro His Val Arg Leu Trp Ala Lys Leu Glu Asp Arg Asn Pro Thr Gly
        35                  40                  45

Ser Ile Lys Asp Arg Pro Ala Leu Arg Met Ile Glu Gln Ala Glu Arg
    50                  55                  60

Asp Gly Leu Leu Gln Pro Gly Ala Thr Ile Leu Glu Pro Thr Ser Gly
65                  70                  75                  80

Asn Thr Gly Ile Ser Leu Ala Met Ala Ala Leu Leu Lys Gly Tyr Asn
                85                  90                  95

Met Ile Cys Val Met Pro Glu Asn Thr Ser Ile Glu Arg Arg Gln Ile
            100                 105                 110

Leu Glu Leu Tyr Gly Ala Arg Ile Ile Phe Ser Pro Ala Glu Gly Gly
        115                 120                 125

Ser Asn Thr Ala Val Ala Thr Ala Lys Glu Leu Ala Ala Gln Asn Pro
    130                 135                 140

Ser Trp Val Met Leu Tyr Gln Tyr Gly Asn Pro Ala Asn Ser Asp Ala
145                 150                 155                 160

His Tyr Phe Gly Thr Gly Pro Glu Leu Leu Ala Asp Leu Pro Glu Ile
```

-continued

```
                165                 170                 175

Thr His Phe Val Ala Gly Leu Gly Thr Thr Gly Thr Leu Met Gly Thr
            180                 185                 190

Gly Arg Phe Leu Arg Glu His Val Pro Gly Val Gln Ile Val Ala Ala
        195                 200                 205

Glu Pro Arg Tyr Gly Glu Gly Val Tyr Ala Leu Arg Asn Ile Asp Glu
    210                 215                 220

Gly Phe Ile Pro Glu Leu Tyr Asp Ala Asp Val Leu Thr Thr Arg Phe
225                 230                 235                 240

Ser Val Gly Ser Phe Asp Ala Val Arg Arg Thr Arg Glu Leu Val Thr
                245                 250                 255

Arg Glu Gly Ile Phe Ala Gly Ile Ser Thr Gly Ala Val Leu His Ala
            260                 265                 270

Ala Leu Gly Met Ala Ala Lys Ala Val Lys Ala Gly Glu Arg Ala Asp
        275                 280                 285

Ile Ala Phe Val Val Ala Asp Ala Gly Trp Lys Tyr Leu Ser Thr Gly
    290                 295                 300

Ala Tyr Ala Gly Ser Leu Asp Asp Ala Glu Asp Ala Leu Glu
305                 310                 315


<210> SEQ ID NO 3
<211> LENGTH: 318
<212> TYPE: PRT
<213> ORGANISM: Artificial Sequence
<220> FEATURE:
<223> OTHER INFORMATION: Msm-T-HA2 from Mycobacterium smegmatics CC1

<400> SEQUENCE: 3

Met Thr Arg Tyr Asp Ser Leu Leu Gln Ala Leu Gly Asn Thr Pro Leu
  1               5                  10                  15

Val Gly Leu Gln Asn Leu Ser Pro Arg Trp Asp Asp Glu Asp Gly Lys
            20                  25                  30

Pro His Val Arg Leu Trp Ala Lys Leu Glu Asp Arg Asn Pro Thr Gly
         35                  40                  45

Ser Ile Lys Asp Arg Pro Ala Leu Arg Met Ile Glu Gln Ala Glu Arg
     50                  55                  60

Asp Gly Leu Leu Gln Pro Gly Ala Thr Ile Leu Glu Ser Thr Ser Gly
 65                  70                  75                  80

Asn Thr Gly Ile Ser Leu Ala Met Ala Ala Leu Leu Lys Gly Tyr Asn
                 85                  90                  95

Met Ile Cys Val Met Pro Glu Asn Thr Ser Ile Glu Arg Arg Gln Ile
            100                 105                 110

Leu Glu Leu Tyr Gly Ala Arg Ile Ile Phe Ser Pro Ala Glu Gly Gly
        115                 120                 125

Ser Asn Thr Ala Val Ala Thr Ala Lys Glu Leu Ala Ala Gln Asn Pro
    130                 135                 140

Ser Trp Val Met Leu Tyr Gln Tyr Gly Asn Pro Ala Asn Ser Asp Ala
145                 150                 155                 160

His Tyr Phe Gly Thr Gly Pro Glu Leu Leu Ala Asp Leu Pro Glu Ile
                165                 170                 175

Thr His Phe Val Ala Gly Leu Gly Thr Thr Gly Thr Leu Met Gly Thr
            180                 185                 190

Gly Arg Phe Leu Arg Glu His Val Pro Gly Val Gln Ile Val Ala Ala
        195                 200                 205

Glu Pro Arg Tyr Gly Glu Gly Val Tyr Ala Leu Arg Asn Ile Asp Glu
```

```
    210                 215                 220

Gly Phe Ile Pro Glu Leu Tyr Asp Ala Asp Val Leu Thr Thr Arg Phe
225                 230                 235                 240

Ser Val Gly Ser Phe Asp Ala Val Arg Arg Thr Arg Glu Leu Val Thr
                245                 250                 255

Arg Glu Gly Ile Phe Ala Gly Ile Ser Thr Gly Ala Val Leu His Ala
            260                 265                 270

Ala Leu Gly Met Ala Ala Lys Ala Val Lys Ala Gly Glu Arg Ala Asp
        275                 280                 285

Ile Ala Phe Val Val Ala Asp Ala Gly Trp Lys Tyr Leu Ser Thr Gly
    290                 295                 300

Ala Tyr Ala Gly Ser Leu Asp Asp Ala Glu Asp Ala Leu Glu
305                 310                 315


<210> SEQ ID NO 4
<211> LENGTH: 318
<212> TYPE: PRT
<213> ORGANISM: Artificial Sequence
<220> FEATURE:
<223> OTHER INFORMATION: Msm-T-EP3 from Mycobacterium smegmatics CC2

<400> SEQUENCE: 4

Met Thr Arg Tyr Asp Ser Leu Leu Gln Ala Leu Gly Asn Thr Pro Leu
  1               5                  10                  15

Val Gly Leu Gln Asn Leu Ser Pro Arg Trp Asp Asp Glu Asp Gly Lys
            20                  25                  30

Pro His Val Arg Leu Trp Ala Lys Leu Glu Asp Arg Asn Pro Thr Gly
        35                  40                  45

Ser Ile Lys Asp Arg Pro Ala Leu Arg Met Ile Glu Gln Ala Glu Arg
     50                  55                  60

Asp Gly Leu Leu Gln Pro Gly Ala Thr Ile Leu Glu Pro Thr Ser Gly
 65                  70                  75                  80

Asn Thr Gly Ile Ser Leu Ala Met Ala Ala Leu Leu Lys Gly Tyr Asn
                85                  90                  95

Met Ile Cys Val Met Pro Glu Asn Thr Ser Ile Glu Arg Arg Gln Ile
            100                 105                 110

Leu Glu Leu Tyr Gly Ala Arg Ile Ile Phe Ser Pro Ala Glu Gly Gly
        115                 120                 125

Ser Asn Ala Ala Val Ala Thr Ala Asp Glu Leu Ala Ala Gln Asn Pro
    130                 135                 140

Ser Trp Val Met Leu Tyr Gln Tyr Gly Asn Pro Ala Asn Ser Asp Ala
145                 150                 155                 160

His Tyr Phe Gly Thr Gly Pro Glu Leu Leu Ala Asp Leu Pro Glu Ile
                165                 170                 175

Thr His Phe Val Ala Gly Leu Gly Thr Thr Gly Thr Leu Met Gly Thr
            180                 185                 190

Gly Arg Phe Leu Arg Glu His Val Pro Gly Val Gln Ile Val Ala Ala
        195                 200                 205

Glu Pro Arg Tyr Gly Glu Gly Val Tyr Ala Leu Arg Asn Ile Asp Glu
    210                 215                 220

Gly Phe Ile Pro Glu Leu Tyr Asp Ala Asp Val Leu Thr Ser Arg Phe
225                 230                 235                 240

Ser Val Gly Ser Phe Asp Ala Val Arg Arg Thr Arg Glu Leu Val Thr
                245                 250                 255

Arg Glu Gly Ile Phe Ala Gly Ile Ser Thr Gly Ala Val Leu His Ala
```

```
            260                 265                 270

Ala Leu Gly Met Ala Ala Lys Ala Val Lys Ala Gly Glu Arg Ala Asp
        275                 280                 285

Ile Ala Phe Val Val Ala Asp Ala Gly Trp Lys Tyr Leu Ser Thr Gly
    290                 295                 300

Ala Tyr Ala Gly Ser Leu Asp Asp Ala Glu Asp Ala Leu Glu
305                 310                 315


<210> SEQ ID NO 5
<211> LENGTH: 318
<212> TYPE: PRT
<213> ORGANISM: Artificial Sequence
<220> FEATURE:
<223> OTHER INFORMATION: Mtb-T from Mycobacterium tuberculosis H37Rv

<400> SEQUENCE: 5

Met Thr Arg Tyr Asp Ser Leu Leu Gln Ala Leu Gly Asn Thr Pro Leu
  1               5                  10                  15

Val Gly Leu Gln Arg Leu Ser Pro Arg Trp Asp Asp Gly Arg Asp Gly
            20                  25                  30

Pro His Val Arg Leu Trp Ala Lys Leu Glu Asp Arg Asn Pro Thr Gly
        35                  40                  45

Ser Ile Lys Asp Arg Pro Ala Val Arg Met Ile Glu Gln Ala Glu Ala
     50                  55                  60

Asp Gly Leu Leu Arg Pro Gly Ala Thr Ile Leu Glu Pro Thr Ser Gly
 65                  70                  75                  80

Asn Thr Gly Ile Ser Leu Ala Met Ala Ala Arg Leu Lys Gly Tyr Arg
                85                  90                  95

Leu Ile Cys Val Met Pro Glu Asn Thr Ser Val Glu Arg Arg Gln Leu
            100                 105                 110

Leu Glu Leu Tyr Gly Ala Gln Ile Ile Phe Ser Ala Ala Glu Gly Gly
        115                 120                 125

Ser Asn Thr Ala Val Ala Thr Ala Lys Glu Leu Ala Ala Thr Asn Pro
    130                 135                 140

Ser Trp Val Met Leu Tyr Gln Tyr Gly Asn Pro Ala Asn Thr Asp Ser
145                 150                 155                 160

His Tyr Cys Gly Thr Gly Pro Glu Leu Leu Ala Asp Leu Pro Glu Ile
                165                 170                 175

Thr His Phe Val Ala Gly Leu Gly Thr Thr Gly Thr Leu Met Gly Thr
            180                 185                 190

Gly Arg Phe Leu Arg Glu His Val Ala Asn Val Lys Ile Val Ala Ala
        195                 200                 205

Glu Pro Arg Tyr Gly Glu Gly Val Tyr Ala Leu Arg Asn Met Asp Glu
    210                 215                 220

Gly Phe Val Pro Glu Leu Tyr Asp Pro Glu Ile Leu Thr Ala Arg Tyr
225                 230                 235                 240

Ser Val Gly Ala Val Asp Ala Val Arg Arg Thr Arg Glu Leu Val His
                245                 250                 255

Thr Glu Gly Ile Phe Ala Gly Ile Ser Thr Gly Ala Val Leu His Ala
            260                 265                 270

Ala Leu Gly Val Gly Ala Gly Ala Leu Ala Ala Gly Glu Arg Ala Asp
        275                 280                 285

Ile Ala Leu Val Val Ala Asp Ala Gly Trp Lys Tyr Leu Ser Thr Gly
    290                 295                 300

Ala Tyr Ala Gly Ser Leu Asp Asp Ala Glu Thr Ala Leu Glu
```

-continued

```
305                 310                 315


<210> SEQ ID NO 6
<211> LENGTH: 389
<212> TYPE: PRT
<213> ORGANISM: Artificial Sequence
<220> FEATURE:
<223> OTHER INFORMATION: Ape-OPSS from Aeropyrum pernix (Synthetic DNA)

<400> SEQUENCE: 6

Met Ala Leu Ala Asp Ile Ser Gly Tyr Leu Asp Val Leu Asp Ser Val
  1               5                  10                  15

Arg Gly Phe Ser Tyr Leu Glu Asn Ala Arg Glu Val Leu Arg Ser Gly
             20                  25                  30

Glu Ala Arg Cys Leu Gly Asn Pro Arg Ser Glu Pro Glu Tyr Val Lys
         35                  40                  45

Ala Leu Tyr Val Ile Gly Ala Ser Arg Ile Pro Val Gly Asp Gly Cys
     50                  55                  60

Ser His Thr Leu Glu Glu Leu Gly Val Phe Asp Ile Ser Val Pro Gly
 65                  70                  75                  80

Glu Met Val Phe Pro Ser Pro Leu Asp Phe Phe Glu Arg Gly Lys Pro
                 85                  90                  95

Thr Pro Leu Val Arg Ser Arg Leu Gln Leu Pro Asn Gly Val Arg Val
            100                 105                 110

Trp Leu Lys Leu Glu Trp Tyr Asn Pro Phe Ser Leu Ser Val Lys Asp
        115                 120                 125

Arg Pro Ala Val Glu Ile Ile Ser Arg Leu Ser Arg Arg Val Glu Lys
    130                 135                 140

Gly Ser Leu Val Ala Asp Ala Thr Ser Ser Asn Phe Gly Val Ala Leu
145                 150                 155                 160

Ser Ala Val Ala Arg Leu Tyr Gly Tyr Arg Ala Arg Val Tyr Leu Pro
                165                 170                 175

Gly Ala Ala Glu Glu Phe Gly Lys Leu Leu Pro Arg Leu Leu Gly Ala
            180                 185                 190

Gln Val Ile Val Asp Pro Glu Ala Pro Ser Thr Val His Leu Leu Pro
        195                 200                 205

Arg Val Met Lys Asp Ser Lys Asn Glu Gly Phe Val His Val Asn Gln
    210                 215                 220

Phe Tyr Asn Asp Ala Asn Phe Glu Ala His Met Arg Gly Thr Ala Arg
225                 230                 235                 240

Glu Ile Phe Val Gln Ser Arg Arg Gly Gly Leu Ala Leu Arg Gly Val
                245                 250                 255

Ala Gly Ser Leu Gly Thr Ser Gly His Met Ser Ala Ala Ala Phe Tyr
            260                 265                 270

Leu Gln Ser Val Asp Pro Ser Ile Arg Ala Val Leu Val Gln Pro Ala
        275                 280                 285

Gln Gly Asp Ser Ile Pro Gly Ile Arg Arg Val Glu Thr Gly Met Leu
    290                 295                 300

Trp Ile Asn Met Leu Asp Ile Ser Tyr Thr Leu Ala Glu Val Thr Leu
305                 310                 315                 320

Glu Glu Ala Met Glu Ala Val Val Glu Val Ala Arg Ser Asp Gly Leu
                325                 330                 335

Val Ile Gly Pro Ser Gly Gly Ala Ala Val Lys Ala Leu Ala Lys Lys
            340                 345                 350

Ala Ala Glu Gly Asp Leu Glu Pro Gly Asp Tyr Val Val Val Val Pro
```

-continued

```
        355                 360                 365

Asp Thr Gly Phe Lys Tyr Leu Ser Leu Val Gln Asn Ala Leu Glu Gly
    370                 375                 380

Ala Gly Asp Ser Val
385


<210> SEQ ID NO 7
<211> LENGTH: 29
<212> TYPE: DNA
<213> ORGANISM: Artificial Sequence
<220> FEATURE:
<223> OTHER INFORMATION: forward primer for Ape-OPSS from Aeropyrum
      pernix (Synthetic DNA)

<400> SEQUENCE: 7

gtcatatgat ggctctggct gacatctct                                       29


<210> SEQ ID NO 8
<211> LENGTH: 29
<212> TYPE: DNA
<213> ORGANISM: Artificial Sequence
<220> FEATURE:
<223> OTHER INFORMATION: reverse primer for Ape-OPSS from Aeropyrum
      pernix (Synthetic DNA)

<400> SEQUENCE: 8

gtaagctttt aaacagagtc accagcacc                                       29


<210> SEQ ID NO 9
<211> LENGTH: 29
<212> TYPE: DNA
<213> ORGANISM: Artificial Sequence
<220> FEATURE:
<223> OTHER INFORMATION: forward primer for Mtb-OPSS Mycobacterium
      tuberculosis H37Rv

<400> SEQUENCE: 9

gtcatatgat gacacgatac gactcgctg                                       29


<210> SEQ ID NO 10
<211> LENGTH: 29
<212> TYPE: DNA
<213> ORGANISM: Artificial Sequence
<220> FEATURE:
<223> OTHER INFORMATION: reverse primer for Mtb-OPSS from Mycobacterium
      tuberculosis H37Rv

<400> SEQUENCE: 10

gtaagctttc atgcccatag ttgcccttc                                       29


<210> SEQ ID NO 11
<211> LENGTH: 29
<212> TYPE: DNA
<213> ORGANISM: Artificial Sequence
<220> FEATURE:
<223> OTHER INFORMATION: forward primer for Msm-OPSS from Mycobacterium
      smegmatics str. MC2 155

<400> SEQUENCE: 11

ataagctttc atgcccatag ctgcccttc                                       29


<210> SEQ ID NO 12
<211> LENGTH: 29
<212> TYPE: DNA
<213> ORGANISM: Artificial Sequence
<220> FEATURE:
```

<223> OTHER INFORMATION: reverse primer for Msm-OPSS from Mycobacterium smegmatics str. MC2 155

<400> SEQUENCE: 12
ataagctttc attccagcgc gtcctcggc 29

<210> SEQ ID NO 13
<211> LENGTH: 29
<212> TYPE: DNA
<213> ORGANISM: Artificial Sequence
<220> FEATURE:
<223> OTHER INFORMATION: forward primer for Rjo-OPSS from Synthetic DNA

<400> SEQUENCE: 13
gtcatatgat ggcgcggttc gattcgctg 29

<210> SEQ ID NO 14
<211> LENGTH: 31
<212> TYPE: DNA
<213> ORGANISM: Artificial Sequence
<220> FEATURE:
<223> OTHER INFORMATION: reverse primer for Rjo-OPSS from Synthetic DNA

<400> SEQUENCE: 14
tagcggccgc tcatgcccac aactgccctt c 31

<210> SEQ ID NO 15
<211> LENGTH: 29
<212> TYPE: DNA
<213> ORGANISM: Artificial Sequence
<220> FEATURE:
<223> OTHER INFORMATION: forward primer for Nfa-OPSS from Synthetic DNA

<400> SEQUENCE: 15
gtcatatgat ggcacgctac gaatcgctg 29

<210> SEQ ID NO 16
<211> LENGTH: 28
<212> TYPE: DNA
<213> ORGANISM: Artificial Sequence
<220> FEATURE:
<223> OTHER INFORMATION: reverse primer for Nfa-OPSS from Synthetic DNA

<400> SEQUENCE: 16
gtaagctttc aggcccagag ctggcctt 28

<210> SEQ ID NO 17
<211> LENGTH: 29
<212> TYPE: DNA
<213> ORGANISM: Artificial Sequence
<220> FEATURE:
<223> OTHER INFORMATION: forward primer for Mtb-T from Mycobacterium tuberculosis H37Rv

<400> SEQUENCE: 17
gtcatatgat gacacgatac gactcgctg 29

<210> SEQ ID NO 18
<211> LENGTH: 29
<212> TYPE: DNA
<213> ORGANISM: Artificial Sequence
<220> FEATURE:
<223> OTHER INFORMATION: reverse primer for Mtb-T from Mycobacterium tuberculosis H37Rv

<400> SEQUENCE: 18
gtaagctttc attccagagc ggtctcggc 29

<210> SEQ ID NO 19
<211> LENGTH: 29
<212> TYPE: DNA
<213> ORGANISM: Artificial Sequence
<220> FEATURE:
<223> OTHER INFORMATION: forward primer for Msm-T, Msm-HA2, Msm-EP3 from Mycobacterium smegmatics str. MC2 155

<400> SEQUENCE: 19
gtcatatgat gacgcgctac gactccctg 29

<210> SEQ ID NO 20
<211> LENGTH: 29
<212> TYPE: DNA
<213> ORGANISM: Artificial Sequence
<220> FEATURE:
<223> OTHER INFORMATION: reverse primer for Msm-T, Msm-HA2, Msm-EP3 from Mycobacterium smegmatics str. MC2 155

<400> SEQUENCE: 20
ataagctttc attccagcgc gtcctcggc 29

<210> SEQ ID NO 21
<211> LENGTH: 21
<212> TYPE: DNA
<213> ORGANISM: Artificial Sequence
<220> FEATURE:
<223> OTHER INFORMATION: forward primer of pCL-P(CJ1)-Msm-T from Mycobacterium smegmatics str. MC2 155

<400> SEQUENCE: 21
gatatcgcag cagccatcat c 21

<210> SEQ ID NO 22
<211> LENGTH: 28
<212> TYPE: DNA
<213> ORGANISM: Artificial Sequence
<220> FEATURE:
<223> OTHER INFORMATION: reverse primer of pCL-P(CJ1)-Msm-T from Mycobacterium smegmatics str. MC2 155

<400> SEQUENCE: 22
cccaagcttt cattccagcg cgtcctcg 28

<210> SEQ ID NO 23
<211> LENGTH: 972
<212> TYPE: DNA
<213> ORGANISM: Artificial Sequence
<220> FEATURE:
<223> OTHER INFORMATION: Msm-OPSS from Mycobacterium smegmatics str. MC2 155

<400> SEQUENCE: 23
atgacgcgct acgactccct gctgcaggcc ctgggcaaca ccccgctggt gggcctgcag 60
aacctgtcgc cccggtggga cgacgaggac gggaaacccc acgtgcggct gtgggccaag 120
ctcgaggacc gcaacccgac cggttccatc aaggaccgcc ccgcgctgcg gatgatcgaa 180
caggccgagc gcgacgggct gctgcagccc ggcgccacga tcctggaacc caccagcggc 240
aacaccggca tctcgctggc catggcggcc ctgctcaagg gctacaacat gatctgcgtg 300
atgccggaga acacgtcgat cgaacggcgc cagatcctcg agctctacgg cgcgcgcatc 360
atcttcagcc ccgccgaggg cggctccaac accgcggtcg cgaccgcgaa agagcttgcc 420

-continued

```
gcgcagaacc cgtcgtgggt catgctgtat cagtacggca acccggccaa cagcgatgcg    480

cactacttcg gcaccggccc cgaactgctc gcggacctgc ccgagatcac ccacttcgtc    540

gcggggctcg gcaccaccgg gaccctgatg ggcaccggac gtttcctgcg cgagcacgtt    600

cccggcgtgc agatcgtggc ggccgaaccg cgttacggcg agggcgtgta cgcactgcgc    660

aacatcgacg agggcttcat ccccgagttg tacgacgccg acgtgctcac cacccggttc    720

tcggtgggct cgttcgacgc cgtgcgccgc acccgtgaac tcgtcacgcg cgagggcata    780

ttcgcgggca tctcgaccgg cgcggtgttg cacgccgcgc tggggatggc cgccaaggcc    840

gtcaaggccg gtgagcgtgc cgacatcgcg ttcgtcgtcg ccgacgccgg atggaagtat    900

ctgtcgaccg gcgcgtacgc cggtagcctg gatgacgccg aggacgcgct ggaagggcag    960

ctatgggcat ga                                                        972
```

<210> SEQ ID NO 24
<211> LENGTH: 954
<212> TYPE: DNA
<213> ORGANISM: Artificial Sequence
<220> FEATURE:
<223> OTHER INFORMATION: Msm-T from Mycobacterium smegmatics str. MC2 155

<400> SEQUENCE: 24

```
atgacgcgct acgactccct gctgcaggcc ctgggcaaca ccccgctggt gggcctgcag     60

aacctgtcgc cccggtggga cgacgaggac gggaaacccc acgtgcggct gtgggccaag    120

ctcgaggacc gcaacccgac cggttccatc aaggaccgcc ccgcgctgcg gatgatcgaa    180

caggccgagc gcgacgggct gctgcagccc ggcgccacga tcctggaacc caccagcggc    240

aacaccggca tctcgctggc catggcggcc ctgctcaagg gctacaacat gatctgcgtg    300

atgccggaga acacgtcgat cgaacggcgc cagatcctcg agctctacgg cgcgcgcatc    360

atcttcagcc ccgccgaggg cggctccaac accgcggtcg cgaccgcgaa agagcttgcc    420

gcgcagaacc cgtcgtgggt catgctgtat cagtacggca acccggccaa cagcgatgcg    480

cactacttcg gcaccggccc cgaactgctc gcggacctgc ccgagatcac ccacttcgtc    540

gcggggctcg gcaccaccgg gaccctgatg ggcaccggac gtttcctgcg cgagcacgtt    600

cccggcgtgc agatcgtggc ggccgaaccg cgttacggcg agggcgtgta cgcactgcgc    660

aacatcgacg agggcttcat ccccgagttg tacgacgccg acgtgctcac cacccggttc    720

tcggtgggct cgttcgacgc cgtgcgccgc acccgtgaac tcgtcacgcg cgagggcata    780

ttcgcgggca tctcgaccgg cgcggtgttg cacgccgcgc tggggatggc cgccaaggcc    840

gtcaaggccg gtgagcgtgc cgacatcgcg ttcgtcgtcg ccgacgccgg atggaagtat    900

ctgtcgaccg gcgcgtacgc cggtagcctg gatgacgccg aggacgcgct ggaa          954
```

<210> SEQ ID NO 25
<211> LENGTH: 954
<212> TYPE: DNA
<213> ORGANISM: Artificial Sequence
<220> FEATURE:
<223> OTHER INFORMATION: Msm-T-HA2 from Mycobacterium smegmatics CC1

<400> SEQUENCE: 25

```
atgacgcgct acgactccct gctgcaggcc ctgggcaaca ccccgctggt gggcctgcag     60

aacctgtcgc cccggtggga cgacgaggac gggaaacccc acgtgcggct gtgggccaag    120

ctcgaggacc gcaacccgac cggttccatc aaggaccgcc ccgcgctgcg gatgatcgaa    180
```

-continued

```
caggccgagc gcgacgggct gctgcagccc ggcgccacga tcctggaatc caccagcggc    240

aacaccggca tctcgctggc catggcggcc ctgctcaagg gctacaacat gatctgcgtg    300

atgccggaga acacgtcgat cgaacggcgc cagatcctcg agctctacgg cgcgcgcatc    360

atcttcagcc ccgccgaggg cggctccaac accgcggtcg cgaccgcgaa agagcttgcc    420

gcgcagaacc cgtcgtgggt catgctgtat cagtacggca acccggccaa cagcgatgcg    480

cactacttcg gcaccggccc cgaactgctc gcggacctgc ccgagatcac ccacttcgtc    540

gcggggctcg gcaccaccgg gaccctgatg ggcaccggac gtttcctgcg cgagcacgtt    600

cccggcgtgc agatcgtggc ggccgaaccg cgttacggcg agggcgtgta cgcactgcgc    660

aacatcgacg agggcttcat ccccgagttg tacgacgccg acgtgctcac cacccggttc    720

tcggtgggct cgttcgacgc cgtgcgccgc acccgtgaac tcgtcacgcg cgagggcata    780

ttcgcgggca tctcgaccgg cgcggtgttg cacgccgcgc tggggatggc cgccaaggcc    840

gtcaaggccg gtgagcgtgc cgacatcgcg ttcgtcgtcg ccgacgccgg atggaagtat    900

ctgtcgaccg gcgcgtacgc cggtagcctg gatgacgccg aggacgcgct ggaa          954
```

```
<210> SEQ ID NO 26
<211> LENGTH: 954
<212> TYPE: DNA
<213> ORGANISM: Artificial Sequence
<220> FEATURE:
<223> OTHER INFORMATION: Msm-T-EP3 from Mycobacterium smegmatics CC2

<400> SEQUENCE: 26

atgacgcgct acgactccct gctgcaggcc ctgggcaaca ccccgctggt gggcctgcag     60

aacctgtcgc cccggtggga cgacgaggac gggaaacccc acgtgcggct gtgggccaag    120

ctcgaggacc gcaacccgac cggttccatc aaggaccgcc ccgcgctgcg gatgatcgaa    180

caggccgagc gcgacgggct gctgcagccc ggcgccacga tcctggaacc caccagcggc    240

aacaccggca tctcgctggc catggcggcc ctgctcaagg gctacaacat gatctgcgtg    300

atgccggaga acacgtcgat cgaacggcgc cagatcctcg agctctacgg cgcgcgcatc    360

atcttcagcc ccgccgaggg cggctccaac gccgcggtcg cgaccgcgaa tgagcttgcc    420

gcgcagaacc cgtcgtgggt catgctgtat cagtacggca acccggccaa cagcgatgcg    480

cactacttcg gcaccggccc cgaactgctc gcggacctgc ccgagatcac ccacttcgtc    540

gcggggctcg gcaccaccgg gaccctgatg ggcaccggac gtttcctgcg cgagcacgtt    600

cccggcgtgc agatcgtggc ggccgaaccg cgttacggcg agggcgtgta cgcactgcgc    660

aacatcgacg agggcttcat ccccgagttg tacgacgccg acgtgctcac ctcccggttc    720

tcggtgggct cgttcgacgc cgtgcgccgc acccgtgaac tcgtcacgcg cgagggcata    780

ttcgcgggca tctcgaccgg cgcggtgttg cacgccgcgc tggggatggc cgccaaggcc    840

gtcaaggccg gtgagcgtgc cgacatcgcg ttcgtcgtcg ccgacgccgg atggaagtat    900

ctgtcgaccg gcgcgtacgc cggtagcctg gatgacgccg aggacgcgct ggaa          954
```

O-PHOSPHOSERINE SULFHYDRYLASE MUTANTS AND METHOD FOR PRODUCTION OF CYSTEINE USING THE SAME

CROSS-REFERENCE TO RELATED APPLICATION

This application claims the priority benefit of Korean Patent Application No. 10-2010-0102665, filed Oct. 20, 2010. The contents of this patent application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_003_00US_ST25.txt. The text file is 27 KB, was created on Oct. 20, 2011, and is being submitted electronically via EFS-Web.

Technical Field

The present invention relates to an O-phosphoserine sulfhydrylase (also referred to as "OPSS") mutant which has a *Mycobacterium smegmatis*-derived amino acid sequence corresponding to that of SEQ ID NO: 1 which is deleted three to seven C-terminal amino acid residues. The present invention also relates to a nucleic acid molecule encoding the OPSS mutant, an expression vector carrying the nucleic acid molecule, and a transformant transformed with the expression vector. In addition, the present invention is concerned with a method for the production of cysteine by reacting O-phospho-L-serine (OPS) with a sulfide in the presence of the OPSS mutant.

BACKGROUND ART

L-cysteine is an amino acid that plays an important role in sulfur metabolism in all living organisms. It is used in the biosynthesis of proteins, such as hair keratin, glutathione, biotin, methionine, and other sulfur-containing metabolites as well as serving as a precursor of coenzyme A. In addition, the biosynthesis of cysteine is known to be closely associated with the biosynthesis of other amino acids including L-serine, L-glycine, and L-methionine. Industrially, L-cysteine and its derivatives find applications in a variety of fields including the pharmaceutical industry (for treatment of bronchial diseases), the cosmetics industry (in hair shampoo, compositions for permanent waves, etc.), and the food industry (antioxidants, flavorant enhancers, dough aids, etc.).

Traditionally, L-cysteine was obtained industrially by acid hydrolysis of human hair or animal feathers (Biotechnology of the Amino Acids Production edited by Ko Aida, p 217-223, 1986). However, not only does the production of cysteine from hair or feathers ensure a yield of as low as 7-8%, but also the use of hydrochloric acid or sulfuric acid produces a significant amount of environment polluting waste. Further, consumers may have a strong aversion to extraction from hair or feathers. These problems have caused a push for the development of environmentally friendly production processes of L-cysteine, leading to the fermentation of L-cysteine utilizing microorganisms.

Representative among the microbial production of L-cysteine is the biological conversion of D, L-ATC using a microorganism (Ryu O H, Ju J Y, and Shin C S, Process Biochem., 32:201-209, 1997). This conversion process is, however, difficult to apply industrially due to the low solubility of the precursor D, L-ATC. Another method of L-cysteine production is direct fermentation using *E. coli* (Patent No. EP 0885962B; Wada M and Takagi H, Appl. Microbiol. Biochem., 73:48-54, 2006). Excessive accumulation of L-cysteine within microorganisms incur intracellular toxicity, resulting in the limitation for production of L-cysteine at a high concentration. To overcome this drawback, L-cysteine-exporting proteins were employed, however there have been no significant improvements in productivity.

Referring to the biosynthesis pathway of L-cysteine in bacteria and plants, O-acetyl-serine (OAS) acts as an intermediate precursor providing the carbon backbone of L-cysteine (Kredich N M and Tomkins G M, J. Biol. Chem., 241: 4955-4965, 1966). The enzyme O-acetylserine sulfhydrylase (OASS), using hydrogen sulfide as a sulfur donor, catalyses the conversion of O-acetylserine to S-sulfocysteine and finally to cysteine, releasing acetate. Alternatively, $SO_4$ may be reduced to thiosulfate for use as a sulfur donor in cysteine production (Nakamura T, Kon Y, Iwahashi H, and Eguchi Y, J. Bacteriol., 156: 656-662, 1983). The cysteine biosynthesis pathway via OAS use the two enzymes of serine acetyltransferase (CysE), which catalyzes the conversion of serine to OAS, and cysteine synthase (CysK), which catalyzes the conversion of OAS to cysteine. Notably among them serine acetyltransferase (CysE) is highly sensitive to feedback inhibition by the final product cysteine (Wada M and Takagi H, Appl. Microbiol. Biochem., 73:48-54, 2006). Therefore, an altered enzyme that is insensitive to feedback inhibition is needed, however is difficult to develop.

DISCLOSURE

Technical Problem

Leading to the present invention, intensive and thorough research into the production of L-cysteine at a high yield conducted by the present inventors aimed at overcoming the problems encountered in the prior art, resulted in the finding that there exists O-phosphoserine sulfhydrylase (OPSS) in *Aeropyrum pernix, Mycobacterium tuberculosis*, and *Trichomonas vaginalis* that takes an O-phospho-L-serine (OPS)-specific pathway, rather than the OAS-specific pathway, to synthesize L-cysteine (Mino K and Ishikawa K, FEBS letters, 551: 133-138, 2003; Burns K E, Baumgart S, Dorrestein P C, Zhai H, McLafferty F W, and Begley T P, J. Am. Chem. Soc., 127: 11602-11603, 2005; Westrop G D, Goodall G, Mottram J C, and Coombs G H, J. Biol. Chem., 281: 25062-25075, 2006) and that the OPSS of *M. tuberculosis*, which catalyzes the conversion of OPS to cysteine with the additional enzymes mec+ and cysO, can use $Na_2S$ as a sulfur donor in converting OPS to cysteine even in the absence of the additional enzymes when five C-terminal amino acid residues are removed therefrom (Agren D, Schnell R and Schneider G, FEBS letters, 583: 330-336, 2009).

Technical Solution

It is therefore an object of the present invention to provide an O-phosphoserine sulfhydrylase (also referred to as "OPSS") mutant which has a *Mycobacterium smegmatis*-derived amino acid sequence corresponding to that of SEQ ID NO: 1 which is deleted three to seven C-terminal amino acid residues.

It is another object of the present invention to provide a nucleic acid molecule encoding the OPSS mutant It is a further object of the present invention to provide an expression vector carrying the nucleic acid molecule.

It is still a further object of the present invention to provide a transformant transformed with the expression vector.

It is still another object of the present invention to provide a method for the conversion of O-phospho-L-serine into cysteine with a sulfide in the presence of the OPSS mutant.

Advantageous Effects

As described above, the OPSS mutant with improved enzymatic activity which is essential for the enzymatic conversion of O-phosphoserine into L-cysteine can be used to produce L-cysteine from OPS on mass scale at a high yield in a simple manner.

BEST MODE

Figure 1:
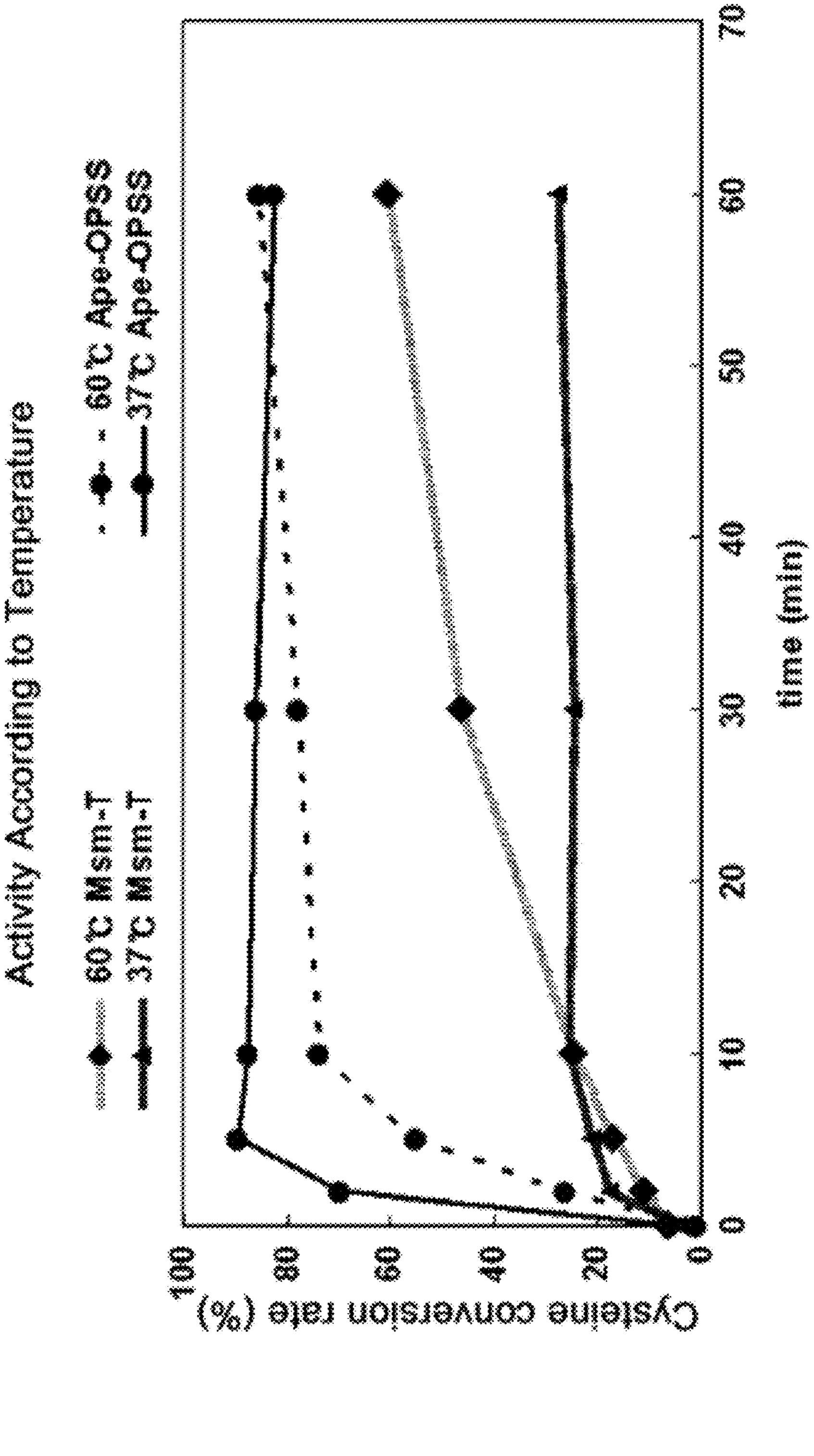
FIG. 1 is a graph showing the activity of OPSS according to temperature.

In accordance with an aspect thereof, the present invention provides a *Mycobacterium smegmatics*-derived OPSS mutant with the same amino acid sequence as that of SEQ ID NO: 1, with the exception of lacking 3 to 7 C-terminal amino acid residues of the wild-type O-phosphoserine sulfhydrylase amino acid sequence.

In one embodiment of the present invention, the OPSS mutant of the present invention may have one of the amino acid sequences of SEQ ID NOS: 2, 3, and 4. The OPSS mutant having an amino acid sequence of SEQ ID NO: 2 may be further modified to have a substitution of the proline residue (Pro) at position 77 with a serine residue (Ser). In addition, the OPSS mutant having an amino acid sequence of SEQ ID NO: 2 may be further modified to have a substitution of the threonine residue (Thr) at position 131 with an alanine residue (Ala), the lysine residue (Lys) at position 137 with an asparagine residue (Asp) and the threonine residue (Thr) at position 238 with a serine residue (Ser). Further, amino acid sequences that share homology of at least 50% preferably 60%, 70%, 75%, and 80%, more preferably 85%, 90% and 95%, and most preferably 97% to 99% with the above-mentioned mutants, fall within the scope of the present invention.

The term "*Mycobacterium smegmatics*" refers to a *bacillus*-shape strain in the phylum Actinobacteria that is fine, straight, or slightly curved, has irregular branches, and can be stained with the basic dye aniline. In the present invention, it was found that when its amino acid sequence was modified, the O-phosphoserine sulfhydrylase derived from the strain could catalyze the biosynthesis of L-cysteine with an increased yield.

As used herein, the term "O-phosphoserine sulfhydrylase (OPSS)" refers to an enzyme that catalyzes the conversion of OPS into cysteine. The enzyme was first found in *Aeropyrum pernix* and named (Mino K and Ishikawa K, FEBS letters, 551: 133-138, 2003, SEQ ID NO: 6).

Various well-known methods may be used to obtain OPSS. Illustrative examples of the methods include, but are not limited to, gene synthesis techniques based on codon optimization by which enzymes of interest can be obtained at a high yield, and bioinformatic screening methods of useful enzyme resources based on massive stores of genetic information of microorganisms. In one embodiment of the present invention, OPSS enzymes that utilize OPS as a substrate to synthesize cysteine were selected from various microbes. In this regard, cell pellets obtained using suitable medium and culture conditions known in the art were (lyzed), followed by the purification of the supernatant containing the enzyme to afford the OPSS enzyme.

As used herein, the term "mutant" refers to a culture or an individual that shows a heritable or non-heritable stable alteration in phenotype. When used in conjunction with OPSS(O-phosphoserine sulfhydrylase), the term "mutant" is intended to mean an OPSS enzyme that is genetically altered such that its activity can be effectively improved, compared to the wild-type.

On the basis of the report that *Mycobacterium tuberculosis* H37Rv-derived OPSS mutants deleted five C-terminal amino acid residues show increased affinity for an $S^{2-}$ group-containing sulfur source even in the absence of additional enzymes, an OPSS mutant was prepared by deleting five C-terminal amino acid residues from the OPSS of *Mycobacterium smegmatics*. The OPSS mutant according to the present invention may have a *Mycobacterium smegmatis*-derived amino acid sequence corresponding to that of SEQ ID NO: 1 which is deleted three to seven, preferably five, C-terminal amino acid residues.

In one embodiment of the present invention, the mutant having the amino acid sequence of SEQ ID NO: 2 was observed to exhibit a conversion rate of 100% within one hour after it was applied to the conversion of OPS into cysteine (Table 5).

Amino acid substitution may further increase the enzymatic activity of the OPSS mutant of the present invention. As long as it is well known in the art, any method may be used to improve the enzyme. In the present invention, preferably, random mutagenesis was employed to bring about an improvement in the enzymatic activity of the OPSS mutant. In detail, after OPSS was allowed to undergo random mutagenesis, mutants with improved enzyme activity were selected using the screening system developed on the basis of HTS (high-throughput screening) by the present inventors. As a result, the OPSS mutants, Msm-T-HA2 and Msm-T-EP3, which have improved enzymatic activity, were obtained by conducting HTS screening on an Msm-T gene. Msm-T-HA2 is an OPSS mutant that has the same amino acid sequence as SEQ ID NO: 2, with the exception that the proline residue (Pro) at position 77 is substituted with a serine residue (Ser). Msm-T-EP3 is an OPSS mutant that has the same amino acid residue as SEQ ID NO: 2, with the exception that substitution mutation occurs with an alanine residue (Ala) for the threonine residue (Thr) at position 131, with an asparagine residue (Asp) for the lysine residue (Lys) at position 137, and with a serine residue (Ser) for the threonine residue (Thr) at position 238. Preferably, the OPSS mutants Msm-T-

HA2 and Msm-T-EP3 have amino acid sequences represented by SEQ ID NO: 3 and SEQ ID NO: 4, respectively.

In one embodiment of the present invention, both Msm-T-HA2 and Msm-T-EP3 were found to exhibit higher enzymatic activity than that of Msm-T having an amino acid residue of SEQ ID NO: 2 (Tables 5 and 6). In detail, the OPSS mutants Msm-T-HA2 and Msm-T-EP3 were measured to exhibit 5-fold and 1.2-fold increased conversion rates in an early stage of the conversion reaction, compared to the control Msm-T. In addition, even when the Msm-T-HA2 mutant of which cysteine synthesis activity is 4-fold higher than that of the Msm-T enzyme and was used in an amount corresponding to 40% of Msm-T, the final cysteine conversion rate was similar.

The term "homology", as used herein, is intended to refer to the percent of identity between two polypeptides. The correspondence between one sequence to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single strand-specific nuclease, and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.). Such proteins (and their encoding genes) have sequence homology, as reflected by their sequence similarity. However, in common usage and in the instant application, the term "homologous," when modified with an adverb such as "highly," may refer to sequence similarity and may or may not relate to a common evolutionary origin.

As used herein, the term "sequence similarity" in all its grammatical forms refers to the degree of identity or correspondence between nucleic acid or amino acid sequences of proteins that may or may not share a common evolutionary origin. In a specific embodiment, two amino acid sequences are "substantially homologous" or "substantially similar" when at least 21% (preferably at least about 50%, and most preferably about 75%, 90%, 95%, 96%, 97%, or 99%) of the amino acids match over the defined length of the amino acid sequences. Sequences that are substantially homologous can be identified by comparing the sequences using standard software available in sequence data banks, or in a Southern hybridization experiment under, for example, stringent conditions as defined for that particular system. The hybridization conditions defined are within the scope of the art (e.g. Sambrook et al., 1989, infra).

The OPSS mutants of the present invention can catalyze the transfer of a thiol group (SH group) to OPS to produce cysteine. Preferably, the conditions that allow the OPSS mutants of the present invention to exert their optimal activity include i) the presence of 0-2 mM PLP (pyridoxal-5'-phosphate) or 0-100 mM DTT (dithiothreitol) as a cofactor, ii) a reaction temperature of from 25 to 60° C., and iii) pH of from 6.0 to 10.0, but are not limited thereto.

An assay for the enzymatic activity of OPSS that catalyzes the synthesis of cysteine by transferring a thiol group to the OPS substrate was disclosed together with the nomenclature of Ape-OPSS (Ape-O-phosphoserine sulfhydrylase). Particularly, because Ape-OPSS has the activity of converting OAS into cysteine by the transfer of a thiol group, the assay is based on the measurement of the activity of *E. coli* cysteine synthesis enzyme (OASS, O-acetylserine sulphydrylase, EC 4.2.99.8)) (Mino K and Ishikawa K, FEBS letters, 551: 133-138, 2003).

In the assay according to one embodiment of the present invention, PLP, which provides a thiol group for OAS (O-acetylserine) or OPS, serving as a cofactor of OASS or OPSS in the cysteine conversion, is added at a concentration of 0.2 mM. Also, DTT is added not only to prevent the oxidation of air-exposed cysteine into cysteine, but also to quantitate the amount of cysteine already oxidized, thanks to its reducing power. Preferably, when 25 mM DTT or 0.2 mM PLP was added, the cysteine conversion rate was increased by 2.3 times. That is, PLP and DTT have positive influences on the conversion of OPS into cysteine.

The enzymes Ape-OPSS, Mtb-OPSS, and Mtb-T have an optimal reaction temperature of 60° C. or 37° C., with an optimal pH of 7.4, as reported previously (Mino K and Ishikawa K, FEBS letters, 551: 133-138, 2003; Agren D, Schnell R and Schneider G, FEBS letters, 583: 330-336, 2009). Based on the report, the conversion reaction conditions for the OPSS mutants with improved enzymatic activity can be optimized.

In one embodiment of the present invention, the OPSS mutants can catalyze the conversion at a temperature of from 37° C. to 80° C. In detail, the Ape-OPSS enzyme from *Archea* spp., which can grow even at high temperatures, shows a higher enzymatic activity at 60° C. than at 37° C. Also, the high-heat stability of the enzyme itself leads to an optimal temperature of 60° C. On the other hand, Msm-T shows optimal enzymatic activity at 37° C. and is vulnerable to heat treatment at 60° C. The OPSS enzymes were found to retain conversion activity over a pH range of from 6.0 to 10.0. Optimal enzymatic activity was detected at pH7.4 in Ape-OPSS and a pH of 8.0 to 9.0 in Msm-T. Hence, Msm-T is stable over a wider range of pH than is Ape-OPSS.

In accordance with another aspect thereof, the present invention provides a nucleic acid molecule encoding the OPSS mutant.

As used herein, the term "nucleic acid molecule" is intended to encompass DNA and RNA molecules. Nucleotides, which make up the structural units of nucleic acid molecules, include not only naturally occurring nucleotides, but sugar moiety- or base moiety-modified analogues (Scheit, Nucleotide Analogs, John Wiley, New York (1980); Uhlman and Peyman, Chemical Reviews, 90:543-584 (1990)).

In accordance with a further aspect thereof, the present invention provides an expression vector carrying the nucleic acid molecule.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and non-viral vehicles for introducing the nucleic acid into a host cell in vitro, ex vivo, or in vivo. The term "vector" may also include minicircle DNAs. For example, the vector may be a plasmid without bacterial DNA sequences. The removal of bacterial DNA sequences that are rich in CpG regions has been shown to decrease transgene expression silencing and resulting in more persistent expression from plasmid DNA vectors (see e.g., Ehrhardt, A. et al. (2003) Hum Gene Ther 10: 215-25; Yet, N. S. (2002) Mol Ther 5: 731-38; Chen, Z.Y. et al. (2004) Gene Ther 11: 856-64). The term "vector" may also include transposons such as Sleeping Beauty (Izsvak et al. J. MoI. Biol. 302:93-102 (2000)), or artificial chromosomes.

As a vector, the pET system (Novagen) using a T7 promoter is well known in the art. In the present invention, various expression systems known in the art may be used without limitation.

Figure 7:
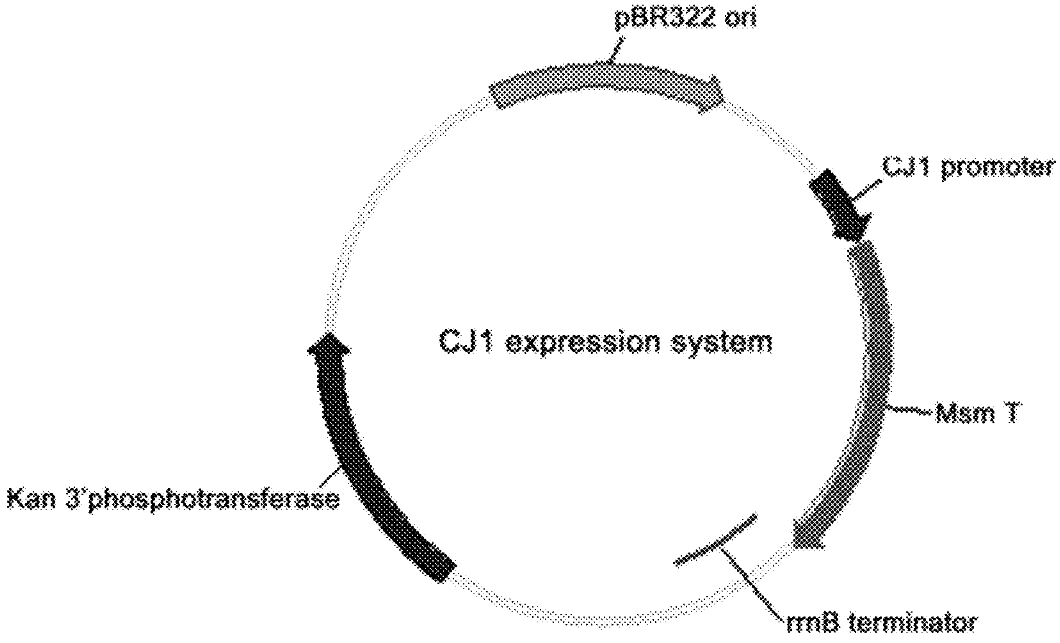
FIG. 7 is a schematic view showing the map of a pCL-Pcj1 expression vector carrying a gene coding for an OPSS mutant.

In one embodiment of the present invention, an expression system using a CJ1 promoter, developed by the present inventors, for expressing an exogenous gene (see, Korean Patent Laid-Open Publication No. 10-2006-0068505, FIG. 7) was employed.

Figure 3:
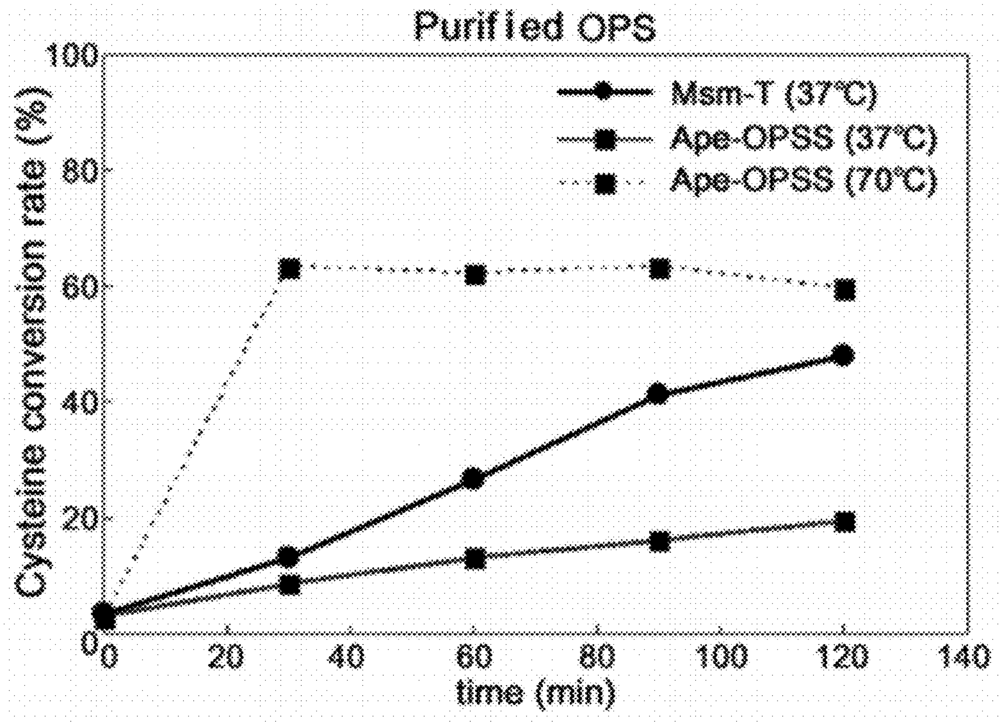
FIG. 3 is a photograph showing the expression level of the enzyme in a pET system and a pCL-Pcj1 system as analyzed by SDS PAGE.

In one embodiment of the present invention, the expression levels of OPSS between the pET system comprising a T7 promoter and the CJ1 system comprising a CJ1 promoter were compared given the same conditions. As a result, the CJ1 system showed a higher expression level of OPSS than did the pET system (FIG. 3). In addition, overexpression of OPSS required a low temperature (18° C.) and a long period of time in the pET system, but a high temperature (37° C.) and a short period of time in the CJ1 system. Therefore, it is preferred that the CJ1 promoter is used to effectively obtain OPSS, but the present invention is not limited thereto.

In accordance with a still further aspect thereof, the present invention provides a transformant transformed with the expression vector.

As used herein, the term "transformation" in all its grammatical forms and spelling variations refers to the artificial genetic alteration of a cell resulting from the introduction of a foreign gene to the host cell so that the introduced gene can replicate itself or as a factor incorporated into the chromosome.

The vector of the present invention can be introduced into host cells by suitable standard techniques known in the art, examples of which include but are not limited to electroporation, calcium phosphate co-precipitation, retroviral infection, microinjection, DEAE-dextran, and cationic liposome calcium.

The term "host cell transformed with a recombinant vector," as used herein, refers to a host cell that anchors a recombinant vector therein carrying a gene of interest. The host cell suitable for use in the present invention may be prokaryotic or eukaryotic. Examples include enterobacteria and coryneform bacteria, with preference for *Escherichia* spp. and *Serratia* spp., with the highest preference being *E. coli.*

In accordance with still another aspect thereof, the present invention provides a method for production of cysteine, comprising of converting OPS with a sulfide in the presence of the OPSS mutant of the present invention.

The mutant of the present invention may be applied to the mass production of cysteine. When the transformant expressing the mutant is used, the mass production of cysteine may be accomplished under optimal culture conditions that are well known in the art. Therefore, the method for mass production of cysteine comprises culturing the transformant in an optimal condition that is well known in the art.

For use as a substrate, OPS may be in pure form or may be in the form of a fermentation culture containing OPS. Pure OPS may be commercially available, as identified in Catalog No. P0878 from Sigma-Aldrich or CAS407-41-0 from Wako. However, the OPS-containing culture obtained by microbial fermentation has economic advantages over commercially available pure OPS in that the OPS-containing culture can be used without additional purification and the cofactor PLP necessary for the conversion can be obtained in the fermented culture.

Any sulfur compound may be used in the present invention, as long as it may be converted to a thiol group (SH). Preferably, $Na_2S$, $H_2S$, or $S_2O_3$, eitherin the form of liquid or gas, may be used.

In one embodiment of the present invention, $Na_2S$ was used as a sulfur source. $Na_2S$ may be added at a molar concentration 0.1 to 3 times as high as that of OPS used in the enzymatic conversion. In detail, Msm-T-HA2, which has a cysteine conversion rate of 80%, which is equivalent to that of Msm-T, is used at a concentration of 50 μg/mL in a reaction condition comprising 50 mM OPS fermentation broth or 60 mM purified OPS fermentation broth, 100 mM or 120 mM $Na_2S$, and 0.2 mM PLP.

Figure 6:
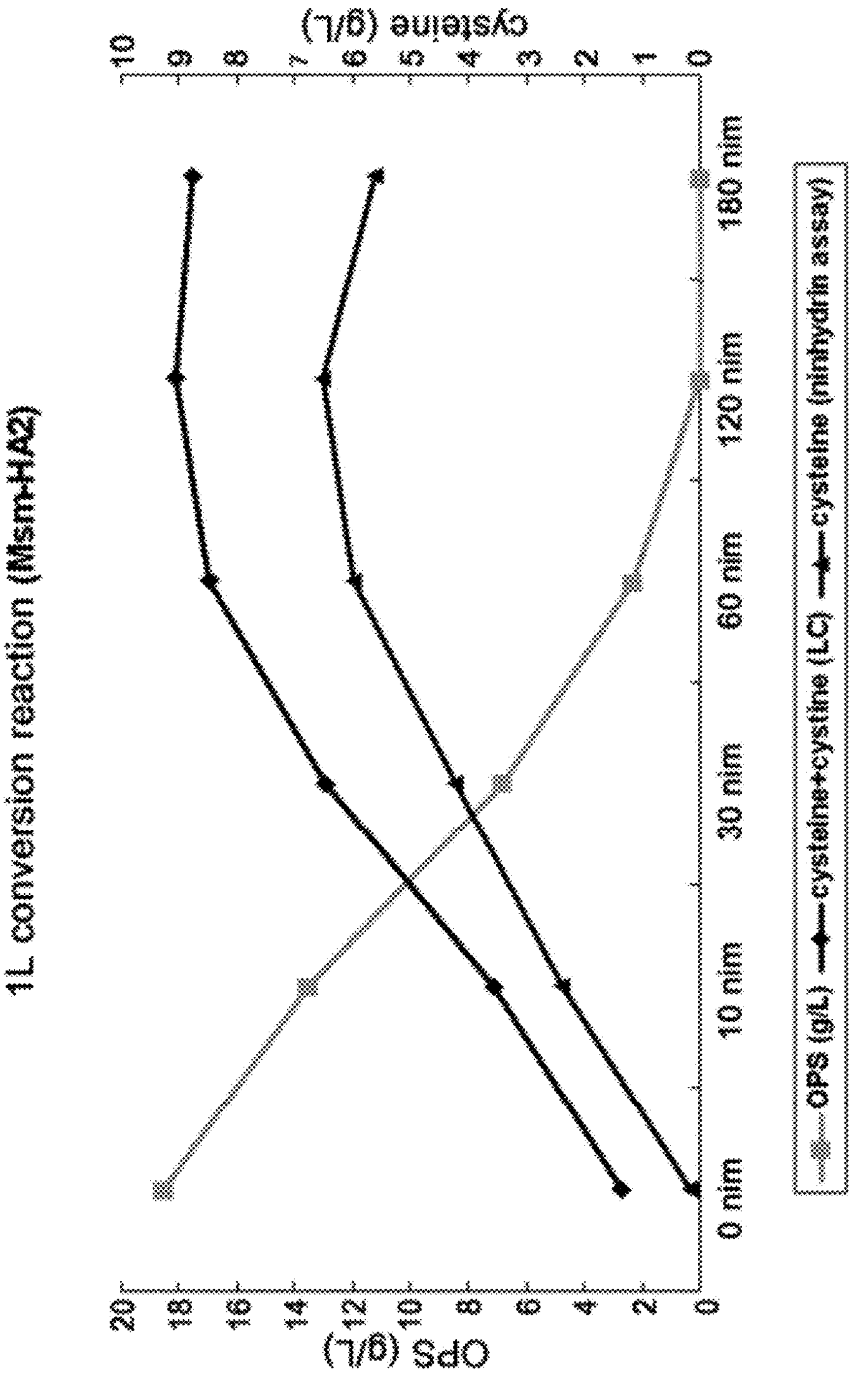
FIG. 6 is a graph showing the production of OPS and cysteine which is converted by OPSS using OPS as a substrate on a 1 L jar scale.

It will be apparent to and readily understood by those skilled in the art that an enzyme conversion process can be optimized and scaled up with highly active enzymes. In one embodiment, when 19.317 g/L OPS fermentation broth was incubated in the presence of 50 mg of Msm-T-HA2, cysteine was produced at a concentration of up to 9.075 g/L. In a 1 L jar, OPS was converted into cysteine at a rate of 71.83% in the presence of the mutant (FIG. 6).

Abbreviation and Terminology

To better explain the present invention and to instruct those technic in the art to perform the present invention, a description is given of the following words and methods. Unless the context clearly requires otherwise, throughout the description and the claims, the words "comprise," "comprising," and the like are to be construed in an inclusive sense as opposed to an exclusive or exhaustive sense, that is to say, in the sense of "including, but not limited to." The singular terms "a," "an," and "the" include plural references unless the context clearly indicates otherwise. For example, the term "comprising a cell" means "including one cell or a plurality of such cells, but not limited thereto."

When used in reference to a list of two or more items, the word "or" covers all of the following interpretations of the word: any of the items in the list, all of the items in the list, and any combination of the items in the list. Unless stated otherwise, all of the technical and scientific terms used herein have the same meanings as are understood to those skilled in the art to which the present invention belongs. Pertinent methods and materials are disclosed below, but similar or equivalent methods and materials may be utilized in the practices or experiments of the present invention. The materials, methods, and examples given below are set forth to illustrate, but are not to be construed as limiting the present invention. Other features and advantages of the present invention will be apparent from the following description and accompanying claims.

Deletion: A mutation in which one or more nucleotides or amino acid residues has been removed from a nucleic acid molecule or a protein, respectively.

MODE FOR INVENTION

A better understanding of the present invention may be obtained through the following examples which are set forth to illustrate, but are not to be construed to limit the present invention.

Example 1

Development of OPSS

*Aeropyrum pernix, Mycobacterium tuberculosis*, and *Trichomonas vaginalis* are reported to have OPSS, an enzyme that use OPS, instead of OAS in *E. coli*, as a substrate for the synthesis of cysteine (Mino K and Ishikawa K, FEBS letters, 551: 133-138, 2003; Burns K E, Baumgart S, Dorrestein P C, Zhai H, McLafferty F W, and Begley T P, J. Am. Chem. Soc., 127: 11602-11603, 2005; Westrop G D, Goodall G, Mottram J C, and Coombs G H, J. Biol. Chem., 281: 25062-25075, 2006). Based on the report, the present inventors found two types of OPSS that convert OPS into cysteine, from *Aeropyrum pernix* and *Mycobacterium tuberculosis* H37Rv. Among them, the *Mycobacterium tuberculosis* H37Rv-derived OPSS enzyme was used for screening amino acid homology. As a result, three OPSS mutants Msm-OPSS, Rjo-OPSS, and Nfa-OPSS were secured from *Mycobacterium smegmatis* str. MC2 155, *Rhodococcus jostii* RHA1, and *Nocardia farcinica* IFM 10152, respectively.

To obtain OPSS from each strain, a pET28a vector system (Novagen), which is typically used for enzyme expression, was constructed. Each templates and primers for use in cloning the five different OPS sulfhydrylase enzymes and the resulting recombinant plasmids are summarized in Table 1, below. Suitable combinations of template and the primers, as given in Table 1, were used for PCR for amplifying each OPSS genes. The PCR products and the pET28a vector were digested with NdeI and HindIII (37° C. for 3 hours). Each of the gene fragments was ligated to the digested pET28a vector (Novagen). Base sequencing confirmed the construction of the expression vectors carrying the each OPSS genes. The enzyme expression vectors were introduced into *E. coli* (DE3) to produce strains capable of expressing five OPSS enzymes. Enzyme names are given in Table 1, below.

TABLE 1

| Enzyme | Vector | Template | Primer |
|---|---|---|---|
| Ape-OPSS | pET28a-Ape-OPSS | Synthetic DNA | SEQ ID NOS: 7 and 8 |
| Mtb-OPSS | pET28a-Mtb-OPSS | Mtb genomic DNA | SEQ ID NOS: 9 and 10 |
| Msm-OPSS | pET28a-Msm-OPSS | Msm genomic DNA | SEQ ID NOS: 11 and 12 |
| Rjo-OPSS | pET28a-Rjo-OPSS | Rjo genomic DNA | SEQ ID NOS: 13 and 14 |
| Nfa-OPSS | pET28a-Nfa-OPSS | Nfa genomic DNA | SEQ ID NOS: 15 and 16 |

Expression of the enzymes was conducted according to the instructions of the pET system manufacturer (Novagen). Single colonies of each strain from the LB plates were inoculated into 5 mL of LB broth and incubated at 37° C. for 16 hours while shaking at 200 rpm. The cultures were transferred to 25 mL of fresh LB broth (in 250 mL flasks) and incubated to an $OD_{600}$ of 0.5~0.6 (for 2~3 hours) in the same condition, immediately after which 1 mM IPTG was added to the media to induce the enzymes to be expressed during incubation at 18° C. for 18 hours while shaking at 120 rpm. The enzymes were purified using Ni-NTA columns for His-tag, with the aid of His SpinTrap (GE Healthcare). Of the five OPSS enzymes isolated, four were found to be in soluble forms, with one (Rjo-OPSS) being an inclusion body, as analyzed by 14% SDS-PAGE electrophoresis.

Example 2

Assay of OPSS for Cysteine Synthesis Activity

The four OPSS enzymes obtained from various microorganism strains were assayed for the ability to catalyze the conversion of OPS to cysteine. With regard to assay conditions and methods (cysM enzyme assay), reference was made to previous reports (Mino K and Ishikawa K, FEBS letters, 551: 133-138, 2003; Burns K E, Baumgart S, Dorrestein P C, Zhai H, McLafferty F W, and Begley T P, J. Am. Chem. Soc., 127: 11602-11603, 2005; Westrop G D, Goodall G, Mottram J C and Coombs G H, J. Biol. Chem., 281: 25062-25075, 2006). The amount of the substrate used is represented by a unit of mL. Assay conditions for enzyme activity are summarized in Table 2, below.

TABLE 2

| Stock sol'n | Final Conc. | Blank | OPS sulfhydrase |
|---|---|---|---|
| 6xhis-enzyme | | — | 40 (50 mg) |
| 1M HEPES (pH 7.4) | 100 mM HEPES | 100 | 100 |
| 0.5M $Na_2S$ | 10 mM $Na_2S$ | 20 | 20 |
| 10 mM PLP | 0.2 mM PLP | 20 | 20 |
| 100 mM OPS | 5 mM OPS | 0 | 50 |
| DW | | 790 | 750 |
| Total | | 1000 | 1000 |

Reaction solutions excepting the enzymes were incubated at 37° C. for 5 min, after which 50 mg of purified OPSS was added to the reaction solution. At predetermined times during incubation at 37° C., 100 mL of the enzyme reactions were taken and mixed with 100 mL of 33.2% TCA to stop the enzymatic reaction. The cysteine concentrations of the enzyme reactions were quantitatively analyzed by measuring absorbance at $OD_{560}$ according to the Gaitonde method. Cysteine synthesis activities of the four different OPS sulfhydrylase enzymes are summarized in Table 3, below. The cysteine synthesis titers of the OPSS enzymes are expressed as cysteine conversion rates with reaction time.

TABLE 3

| | Cysteine Conversion Rate (%) | | |
|---|---|---|---|
| | 10 min | 30 min | 60 min |
| Ape-OPSS | 63.4 | 89.7 | 97.4 |
| Mtb-OPSS | 1.7 | 4.8 | 10.1 |
| Msm-OPSS | 12.8 | 25 | 43.7 |
| Nfa-OPSS | 0.1 | 0.1 | 0.2 |

As can be seen in Table 3, the OPSS enzymes derived from *Aeropyrum pernix* and *Mycobacterium tuberculosis* H37Rv were confirmed to have the activity of using OPS as a substrate to synthesize cysteine. The cysteine synthesis activity of the novel *Mycobacterium smegmatis* str. MC2 155-derived OPSS, which was obtained by screening amino acid homology with the Mtb-OPSS enzyme, was first found. On the other hand, the novel *Nocardia farcinica* IFM 10152-derived OPSS, obtained by the homology screening, exhibited insufficient activity of converting O-phosphoserine into cysteine.

As seen in the data of Table 3, the conversion rate from OPS into cysteine of Ape-OPSS reached near 100% in one hour.

The final conversion rate of the Msm-OPSS enzyme, which was newly selected through enzyme screening on the basis of previously reported *Mycobacterium tuberculosis* H37Rv-derived OPSS, was 43.7% which is 4.3 times as high as that of Mtb-OPSS.

Example 3

Preparation of Mtb-T and Msm-T, Mutants Deleted 5 C-Terminal Amino Acid Residues of Mtb-OPSS and Msm-OPSS

*Mycobacterium tuberculosis* H37Rv-derived OPSS (Mtb-OPSS), which catalyzes the conversion of OPS to cysteine with the aid of the additional enzymes mec+ and cysO, is able to use an $S^{2-}$ containing sulfur source in converting OPS to cysteine even in the absence of the additional enzymes when five C-terminal amino acid residues are removed therefrom. On the basis of this fact, Mtb-T (SEQ ID NO: 24), which can rapidly convert OPS in the presence of $S^{2-}$ as a sulfur source, was obtained. From Msm-OPSS that shares a high amino acid homology with Mtb-OPSS, Msm-T was also obtained by deleting 5 C-terminal amino acid residues. Expression vectors carrying the two enzyme mutants were constructed. In this regard, pfu PCR was performed on the genomic DNA of *Mycobacterium tuberculosis* H37Rv and *Mycobacterium smegmatis* str. MC2 155 in the presence of each pairs of primers of SEQ ID NOS: 17 and 18 and SEQ ID NOS: 19 and 20. The OPSS gene fragments thus obtained were treated with NdeI and HindIII and were cloned into the pET28a vector digested with the same restriction enzymes to construct recombinant expression vectors named pET28a-Mtb-T and pET28a-Msm-T, respectively. The recombinant expression vectors were introduced into *E. coli* (DE3). The expression of the two OPSS mutants obtained under the same condition as in Example 1 was confirmed by 14% SDS PAGE. As a result, Mtb-T (SEQ ID NO: 5) and Msm-T (SEQ ID NO: 2) were obtained.

Example 4

Assay of Mtb-T and Msm-T for Cysteine Synthesis Activity

Mtb-T and Msm-T, obtained above, were evaluated for enzymatic activity by measuring final cysteine conversion rates. Enzymatic activity was assayed in the same manner as in Example 2. The converted cysteine was quantitatively analyzed using the Gaitonde method and the results are summarized in Table 4, below.

TABLE 4

| | Cysteine Conversion Rate (%) | | |
|---|---|---|---|
| | 10 min | 30 min | 60 min |
| Mtb-T | 9.5 | 18.6 | 37.1 |
| Msm-T | 20.3 | 54.6 | 100 |

As seen in Table 4, the Msm-T mutant allowed the conversion of cysteine from the substrate at a rate of 100% in one hour.

Example 5

Assay for Cysteine Synthesis Activity of Msm-T-Derived Mutants Msm-T-HA2 and Msm-T-EP3

On the basis of Msm-T, which can convert OPS into cysteine at a rate of 100%, two enzyme mutants with improved activity were obtained using an enzyme evolutionary method, and named Msm-T-HA2 (SEQ ID NO: 25) and Msm-T-EP3 (SEQ ID NO: 26) Random mutagenesis using hydroxylamine treatment and an error-prone PCR kit (Clontech. Diversity PCR random mutagenesis kit) were introduced into Msm-T to construct a library of Msm-T mutants which were then screened to select OPSS mutants with improved enzymatic activity.

The OPSS mutants Msm-T-HA2 and Msm-T-EP3, obtained by HTS screening on an Msm-T gene, were found to have amino acid sequences of SEQ ID NOS: 3 and 4, respectively, as analyzed by base sequencing.

The mutants Msm-T-HA2 and Msm-T-EP3 and the control Msm-T were assayed for enzymatic activity, and the results are summarized in Table 5 and 6. The enzyme activity assay was conducted in the same manner as in Example 2.

TABLE 5

| | Cysteine Conversion Rate (%) | | |
|---|---|---|---|
| | 10 min | 30 min | 60 min |
| Msm-T | 20.3 | 54.6 | 100 |
| Msm-T-HA2 | 101.6 | 101.2 | 97.5 |
| Msm-T-EP3 | 24 | 65.7 | 100.7 |

TABLE 6

| | Msm-T | Msm-T-HA2 | Msm-T-EP3 |
|---|---|---|---|
| Specific activity (Cysteine (μmole)/min/mg) | 14.96 | 44.82 | 16.72 |

As can be seen in Tables 5 and 6, the OPSS mutants Msm-T-HA2 and Msm-T-EP3, obtained by an enzyme evolutionary method, were measured to exhibit 5-fold and 1.2-fold increased conversion rates, respectively, within 10 min after initiation of the reaction, compared to the control Msm-T. Also, they were compared in terms of specific activity (product concentration/time/enzyme amount), which is widely used in the determination of enzyme activity. The specific activity of Msm-HA2 was three-fold increased compared to that of the control Msm-T, indicating that the OPSS mutant is improved in enzyme activity, with the capacity of synthesizing cysteine in higher amounts per time per unit enzyme.

Example 6

Requirement of Cofactor for OPSS Activity

To examine the effect of cofactors on the cysteine conversion of OPSS, the cysteine conversion rate of Msm-T was measured in the absence or presence of PLP and DTT. In this regard, the substrates of 50 mM OPS broth and 100 mM $Na_2S$ were reacted at 37° C. for 30 min in the presence of 25 mM DTT or 0.2 mM PLP. The cysteine thus produced was quantitatively analyzed using the Gaitonde method. The results are summarized in Table 7, below.

TABLE 7

| Msm-T | Cysteine Conversion Rate (%) |
|---|---|
| (−) PLP, (−) DTT | 23.62 |
| (+) PLP, (−) DTT | 33.21 |
| (−) PLP, (+) DTT | 40.08 |
| (+) PLP, (+) DTT | 54.65 |

As seen in Table 7, the cysteine conversion rate in the presence of both PLP and DTT was 2.3 times as large as that in the absence of both PLP and DTT. Thus, both PLP and DTT were observed to have a positive influence on the conversion.

Example 7

Activity of OPSS by Temperature

The cysteine conversion rates of Ape-OPSS and Msm-T according to temperatures were examined. The enzymatic activity at 37° C. and 60° C. was measured at 2, 5, 10, 30, and 60 min after reaction. The reaction was conducted under the condition of 100 mM HEPES (pH 7.4), 5 mM OPS, 10 mM $Na_2S$, 0.2 mM PLP, and CysM 50 μg/mL. The amount of produced cysteine was determined using the Gaitonde method. The results are shown in FIG. 1.

In the condition of a buffer, as shown in FIG. 1, Ape-OPSS showed a faster initial reaction rate at 37° C. as well as higher reactivity at 60° C. than did Msm-T.

Example 8

Heat Stability of OPSS

Ape-OPSS and Msm-T were analyzed for heat stability. Each of the enzymes was diluted to a concentration of 2 mg/mL in an OPS broth and thermally treated at 37° C. and 60° C. for 10, 30, 60, 120, and 240 min, followed by reaction at 37° C. for 30 min under the condition of 5 mM OPS, 10 mM $Na_2S$, 0.2 mM PLP, and 100 mM HEPES (pH 7.4). For this reaction, 10 μg/mL Ape-OPSS and 50 μg/mL Msm-T were employed. The amounts of the produced cysteine were measured using the Gaitonde method and are summarized in Table 8, below.

TABLE 8

| | Relative activity (%) Heating time (min) | | | | | |
|---|---|---|---|---|---|---|
| | (—) | 10 min | 30 min | 60 min | 120 min | 240 min |
| Ape-OPSS | 100 | 102 | 107 | 100 | 107 | 101 |
| Msm-T | 100 | 82 | 50 | 32 | 19 | 8 |

In spite of heat treatment at 60° C. for 4 hours, as seen in Table 8, Ape-OPSS was observed to retain its activity intact while the activity of Msm-T was maintained at 37° C., but decreased by 50% upon heat treatment at 60° C. for 30 min.

An examination was made on the retention of enzymatic activity at 37° C. when Msm-T was used in an amount of 50 μg/mL, which is a practical concentration in OPS broth. In the absence of $Na_2S$, 50 μg/mL Msm-T was treated, together with 50 mM OPS broth and 0.2 mM PLP, at 37° C. for 0.5, 1, 2, 4, and 6 hours, after which $Na_2S$ was added to induce the enzymatic reaction. After the reaction for 30 min, the activity of Msm-T was measured. The amounts of the produced cysteine were determined using the Gaitonde method and are given in Table 9, below.

TABLE 9

| | Time | | | | | |
|---|---|---|---|---|---|---|
| | (—) | 30 min | 60 min | 120 min | 240 min | 360 min |
| Cysteine Conversion Rate (%) | 100 | 88 | 73 | 47 | 11 | 3 |

As can be seen in Table 9, the activity of Msm-T was decreased below 50% 2 hours after reaction at 37° C. in OPS broth.

Example 9 pH Sensitivity of OPSS

The cysteine conversion rates of Ape-OPSS and Msm-T according to pH were measured. In 100 mM of buffer, Ape-OPSS and Msm-T, each having a concentration of 50 μg/mL, were subjected to reaction at 37° C. for 10 min. In this regard, a K-phosphate buffer with a pH of 6.4/7.0/7.4/8.0, a Tris-HCl buffer with a pH of 7.0/7.4/8.0/8.5/8.8, and a Na-carbonate buffer with a pH of 8.0/8.5/9.0/10.0 were used. The quantitative analysis of the produced cysteine was conducted using the Gaitonde method. The results are summarized in FIG. 2.

Figure 2:
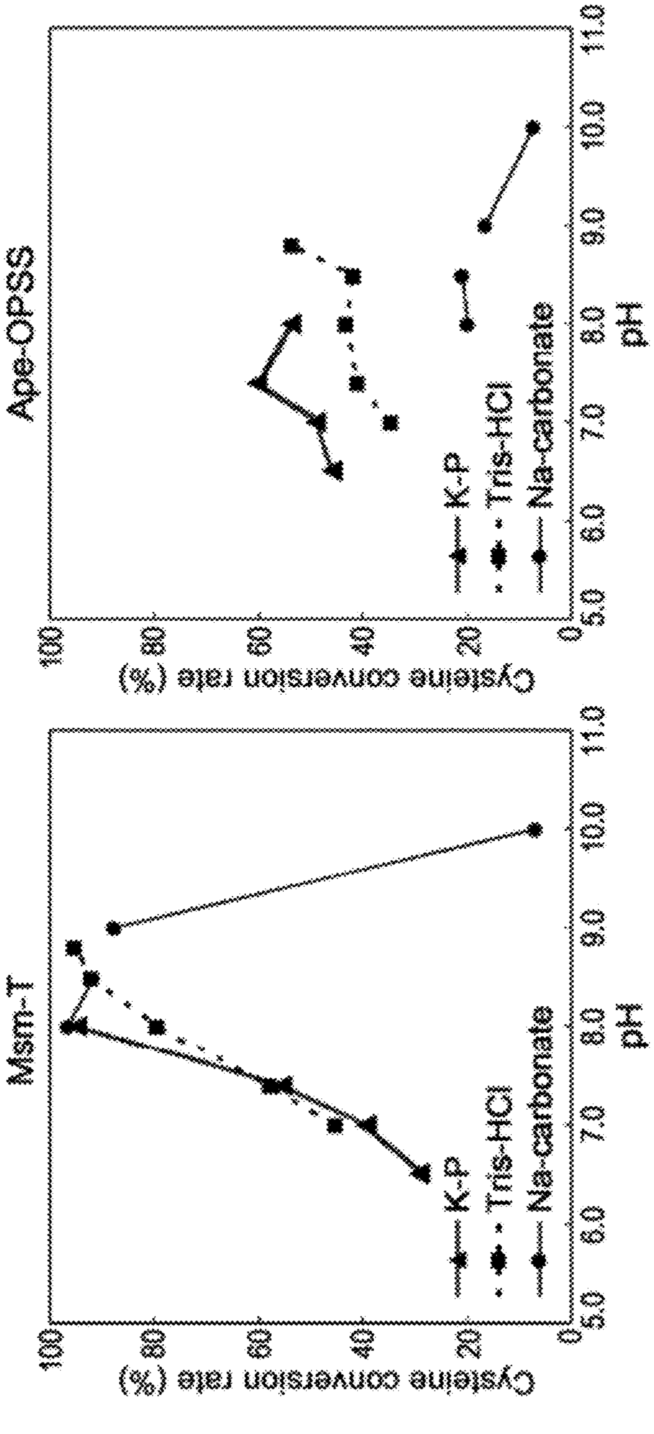
FIG. 2 is a set of graphs showing the pH sensitivity of OPSS.

As seen in FIG. 2, Msm-T exhibited the highest activity at a pH of from 8.0 to 9.0 irrespective of buffer. As for Ape-OPSS, its highest activity was detected in K-phosphate (pH 7.4), with an optimal pH differing from one buffer to another.

Example 10

Effect of Ions on the Activity of OPSS

Effects of ions on the activity of the OPSS enzymes were examined as follows. In a reaction mixture containing 5 mM OPS, 10 mM $Na_2S$, 0.2 mM PLP, and 100 mM HEPES (pH 7.4), the enzymes were subjected to reaction at 37° C. for 30 min in the presence of $(NH_4)_2SO_4$ [1, 3, 5, 10, 20 g/L], $KH_2PO_4$ [0.5, 1, 2, 4, 8 g/L], or $NH_4Cl$ [0.2, 0.5, 1, 2 g/L]. Ape-OPSS and Msm-T were used at a concentration of 10 μg/mL and 50 μg/mL, respectively. The amounts of the produced cysteine were determined using the Gaitonde method and are summarized in Table 10, below.

TABLE 10

| | Relative activity (%) | |
|---|---|---|
| $NH_4Cl$ | Ape-OPSS | Msm-T |
| 0 | 100.00 | 100.00 |
| 0.2 | 86.26 | 91.49 |
| 0.5 | 73.35 | 91.30 |
| 1 | 49.11 | 67.11 |
| 2 | 27.72 | 47.12 |

No changes were detected in the cysteine conversion rate when $(NH_4)_2SO_4$ or $KH_2PO_4$ was added to the reaction mixture. On the other hand, as can be seen in Table 10, the cysteine conversion rate was decreased with an increase in $NH_4Cl$ concentration. Particularly, the maximal enzyme activity was decreased by more than 70% when 2 g/L $NH_4$ was added. Therefore, $NH_4Cl$ and $NH_4$ were observed to have a negative effect on the conversion activity of OPSS.

Example 11

Effect of Sulfur Source on the Cysteine Synthesis Activity of OPSS

An experiment was conducted to examine the effect of sulfur sources on the cysteine synthesis activity of each enzyme. In a reaction mixture containing 5 mM OPS, 0.2 mM PLP, and 100 mM HEPES, each enzyme (50 μg/mL Ape-OPSS, 50 μg/mL Msm-T) was subjected to reaction at 37° C. for 1 hour in the presence of 10 mM $Na_2S$, NaSH, or $Na_2S_2O_3$. The amounts of the produced cysteine were measured using the Gaitonde method. Ape-OPSS was observed to prefer $Na_2S_2O_3$ as a sulfur source, whereas Msm-T prefers $Na_2S$. The results are summarized in Table 11, below.

TABLE 11

| | Relative activity (%) | | |
|---|---|---|---|
| Enzyme | $Na_2S$ | NaSH | $Na_2S_2O_3$ |
| Ape-OPSS | 100.0 | 95.2 | 142.3 |
| Msm-T | 106.7 | 98.3 | 66.2 |

Example 12

Construction of Expression Vector Carrying OPSS (pCL-Pcj1 System) and Expression of the Enzyme PCR was performed using primers of SEQ ID NOS: 21 and 22, with the pET28a-Msm-T vector serving as a template. The PCR product thus obtained was treated with EcoRV and HindIII, and cloned to construct a recombinant vector named pCL-P(CJ1)-Msm-T (pCJ1-MsmT CysM, FIG. 7). To examine a difference in the expression level of Msm-tc between the pET system and the pCL-Pcj1 system, strains for expressing the enzyme were prepared. The pET system was introduced into Rosetta (DE3) while the pCL-Pcj1 system employed the K12G strain. Single colonies taken from LB plates were inoculated into 5 mL of LB broth and cultured at 37° C. for 16 hours while shaking at 200 rpm. These cultures were transferred to 25 mL of fresh LB broth containing kanamycine or spectinomycine and 0.2% glucose (in 250 mL flasks) and incubated to an OD600 of 0.5-0.6, immediately after which 1 mM IPTG was added to the media to induce the enzymes to be expressed. During incubation at 37° C. while shaking at 200 rpm, the expression levels of the enzyme were measured at various culture times (8, 16, 24 hours). The enzyme expression levels of the two systems were analyzed on 14% SDS PAGE and are shown in FIG. 3.

In the same condition, as can be seen in FIG. 3, the pCL-Pcj1 system ensures a higher expression level of the enzyme than does the pET system. In addition, there is an improvement in culture condition because a temperature of as high as 37° C. and an IPTG concentration of as low as 0.1 mM allowed the system to express the enzyme. Therefore, the pCL-Pcj1 system can sufficiently function in substitution for the pET.

Example 13

Cysteine Synthesis of OPSS with the Use of Purified OPS Fermentation Broth as Substrate The conversion rates from purified OPS to cysteine of Msm-T and Ape-OPSS were determined. In the presence of 75 μg/mL of each of the enzymes and 0.2 mM PLP, 60 mM OPS purified from OPS fermentation broth was reacted with 120 mM $Na_2S$ at 37° C. or 70° C. for 30, 60, 90, and 120 min. The reaction was conducted only at 37° C. for Msm-T, but at both 37° C. and 70° C. for Ape-OPSS. The amounts of the produced cysteine were measured using the Gaitonde method. The results are shown in FIG. 4.

Figure 4:
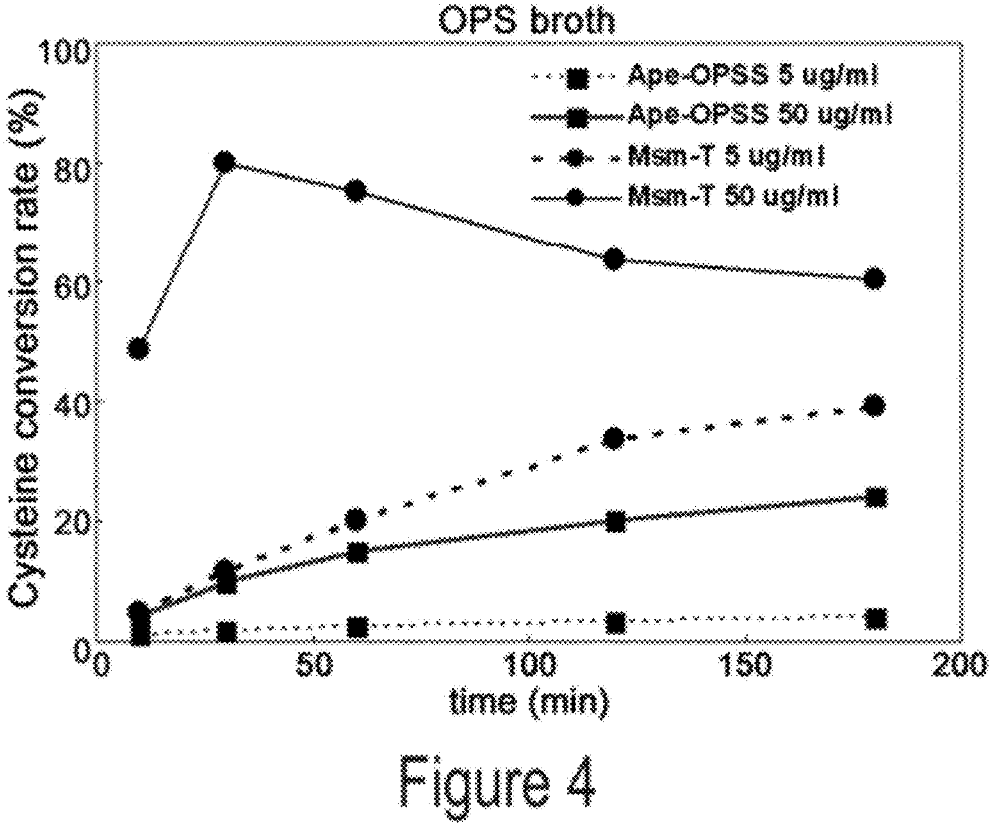
FIG. 4 is a graph showing the enzymatic activity of OPSS to convert purified OPS fermentation broth into cysteine.

As seen in FIG. 4, a purified OPS fermentation broth served well as a substrate for the enzymatic conversion into cysteine. Particularly, the cysteine conversion rate of Ape-OPSS was increased at 70° C. even upon the use of the purified OPS fermentation broth.

Example 14

Cysteine Synthesis of OPSS with the Use of OPS Fermentation Broth as Substrate

When an OPS fermentation broth was used as a substrate, the cysteine conversion rates of Msm-T and Ape-OPSS were measured according to the concentrations of the enzymes. In the presence of 5 μg/mL or 50 μg/mL of each of Msm-T and Ape-OPSS and 0.2 mM PLP, 50 mM of OPS fermentation broth was reacted with 100 mM $Na_2S$ at 37° C. The amounts of the produced cysteine were measured using the Gaitonde method. The results are shown FIG. 5.

Figure 5:
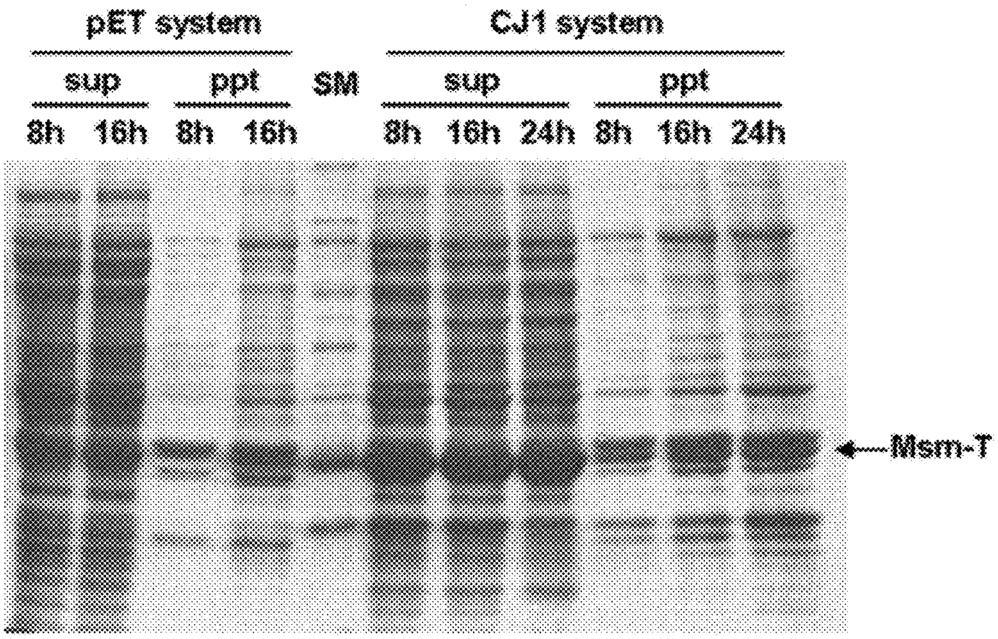
FIG. 5 is a graph showing the enzymatic activity of OPSS to convert OPS fermentation broth into cysteine.

As seen in FIG. 5, the highest conversion rate was detected in 50 μg/mL Msm-T. In addition, upon the use of OPS fermentation broth as a substrate, the activity of Msm-T was higher than that of Ape-OPSS.

Example 15

Cysteine Conversion Rate According to OPSS Concentration

To an OPS broth containing OPS at a concentration of 9.76 g/L, $Na_2S$ was added in an amount twice as large as the mole number of OPS, followed by incubation at 37° C. for 5 min. Thereafter, purified Msm-T was added in an amount of 50 mg while purified Msm-T-HA2 was used in an amount of 5 μg, 10 μg, 20 μg, and 50 μg. At predetermined times during incubation at 37° C., 100 mL of the enzyme reaction mixture was taken and mixed with 100 mL of 33.2% TCA to stop the enzymatic reaction. The cysteine concentrations of the enzyme reactions were quantitatively analyzed by measuring absorbance at $OD_{560}$ according to the Gaitonde method. Cysteine synthesis activities of the OPSS enzymes according to enzyme concentrations are summarized in Table 12, below.

TABLE 12

| | | Cysteine Conversion Rate (%) | | | | |
|---|---|---|---|---|---|---|
| Time | | 0 min | 10 min | 20 min | 30 min | 60 min |
| Msm-T | 50 μg | 0.00 | 20.69 | 48.45 | 62.68 | 59.82 |
| Msm-T-HA2 | 5 μg | 0.00 | 0.00 | 4.77 | 10.66 | 27.23 |
| Msm-T-HA2 | 10 μg | 0.00 | 10.46 | 24.78 | 37.43 | 57.32 |
| Msm-T-HA2 | 20 μg | 0.00 | 14.90 | 31.31 | 48.09 | 59.94 |
| Msm-T-HA2 | 50 μg | 2.33 | 44.02 | 56.72 | 62.17 | 63.52 |

As can be seen in Table 12, even when the Msm-T-HA2 mutant of which cysteine synthesis activity was improved and was used in an amount corresponding to 40% of that of Msm-T, the final cysteine conversion rate (%) was similar. In addition, when used in the same amount, the Msm-T-HA2 mutant showed faster initial reaction activity compared to Msm-T.

Example 16

Cysteine Conversion Rate by OPS Concentrations

To examine the effect of OPS concentration on the conversion rate of Msm-T and Msm-T-HA2, predetermined amounts of purified OPS were added to OPS fermentation broth to induce the conversion reaction. The enzyme was used in an amount of 50 μg for Msm-T and 20 μg for Msm-T-HA2. The amounts of cysteine in the reaction solution were measured using the Gaitonde method. The results are summarized in Tables 13 to 15.

TABLE 13

| Cysteine Conversion Rate (OPS measured 10.65 g/l) | | | | | | |
|---|---|---|---|---|---|---|
| | Time | | | | | |
| | 0 min | 10 min | 30 min | 60 min | 120 min | 180 min |
| Msm-T 50 ug | 0 | 23.03 | 65.38 | 65.70 | 61.95 | 55.35 |
| Msm-T-HA2 20 ug | 0 | 13.70 | 43.82 | 61.32 | 63.77 | 53.74 |

TABLE 14

| Cysteine Conversion Rate (OPS measured 36.09 g/l) | | | | | | |
|---|---|---|---|---|---|---|
| | Time | | | | | |
| | 0 min | 10 min | 30 min | 60 min | 120 min | 180 min |
| Msm-T 50 ug | 0 | 1.15 | 10.23 | 28.07 | 97.84 | 100.34 |
| Msm-T-HA2 20 ug | 0 | 2.33 | 12.04 | 27.57 | 77.65 | 80.01 |

TABLE 15

| Cysteine Conversion Rate (OPS measured 55.6 g/l) | | | | | | |
|---|---|---|---|---|---|---|
| | Time | | | | | |
| | 0 min | 10 min | 30 min | 60 min | 120 min | 180 min |
| Msm-T 50 ug | 0 | 0 | 2.36 | 7.41 | 42.69 | 66.67 |
| Msm-T-HA2 20 ug | 0 | 0.32 | 4.76 | 12.15 | 50.16 | 62.46 |

When the concentration of OPS was about 30 g/L, as seen in Tables 13 to 15, the highest conversion rates were detected as being 100% for Msm-T and 80% for Msm-T-HA2. When the concentration of OPS exceeded 50 g/L, both the conversion rate and the conversion percentage were found to decrease.

The data of Tables 13 to 15 was used to select an optimal concentration ratio between OPS and Msm-T-HA2 for a conversion process using a high concentration of OPS, and to reduce the reaction time of Msm-T-HA2 compared to that of Msm-T.

Example 17

Cysteine Conversion Rate by $Na_2S$ Concentrations

To examine the effect of the amount of $Na_2S$ used as a sulfur source on the cysteine conversion rate, OPS conversion reactions were conducted in the presence of 20 μg of Msm-T-HA2 when $Na_2S$ was used at a concentration of 160 mM, 320 mM, and 480 mM, which corresponded to the amounts equivalent to and twice and three times as large as the mole number of OPS, respectively. The resulting cysteine conversion rates are summarized in Table 16, below.

TABLE 16

| Cysteine Conversion Rate (OPS 29.76 g/l) | | | | | | |
|---|---|---|---|---|---|---|
| | Time | | | | | |
| | 0 min | 10 min | 30 min | 60 min | 120 min | 180 min |
| 160 mM $Na_2S$ | 0 | 0 | 0 | 0 | 0 | 0 |
| 320 mM $Na_2S$ | 0 | 13.43 | 34.58 | 78.78 | 67.76 | 74.95 |
| 480 mM $Na_2S$ | 0 | 14.90 | 25.99 | 54.42 | 51.24 | 58.25 |

As can be seen in Table 16, the cysteine conversion rate peaked when the mole number of $Na_2S$ was twice as large as that of the OPS used. From the results, it is understood that an optimal condition is set when the molar ratio of $Na_2S$ to OPS is 2.

Example 18

Cysteine Conversion Rate by pH

To examine the effect of pH on the enzymatic conversion of OPS into cysteine, a conversion reaction was conducted in the presence of 20 μg of Msm-T-HA2 at various pH values. The results are summarized in Table 17, below.

TABLE 17

| Cysteine Conversion Rate (%) | | | | | |
|---|---|---|---|---|---|
| | Time | | | | |
| | 0 min | 10 min | 30 min | 60 min | 120 min |
| pH 8.5 (OPS 35.02 g/l) | 0.24 | 4.74 | 20.74 | 40.19 | 69.13 |
| pH 9 (OPS 34.59 g/l) | 0.19 | 6.00 | 24.03 | 43.86 | 63.88 |
| pH 9.5 (OPS 35.34 g/l) | 0.26 | 9.85 | 28.48 | 44.82 | 64.68 |
| pH 10 (OPS 34.59 g/l) | 0.25 | 10.97 | 28.54 | 40.19 | 58.14 |

As can be seen, an optimal pH for the conversion reaction was measured to be between 8.5 and 9.5.

Example 19

Conversion Process on 1 L Jar Scale

The reaction process for converting OPS broth into cysteine was scaled up to a 1 L jar. Based on the OPSS characteristics and conversion reaction data set under the 1 mL tube condition, a conversion reaction process was established for Msm-T-HA2.

Preceding a conversion reaction on a 1 L jar scale, OPS fermentation broth obtained in a 1 L jar was centrifuged (10,000 rpm, 10 min, 4° C.) and the supernatant was passed through a membrane (0.45 μm) to remove cells. 72 g of $Na_2S$ was added to the filtered OPS broth (19.317 g/L), followed by filtering out the precipitate through Whatman filter paper (6 μm). After the addition of 10 mM PLP, the reaction mixture was pre-incubated at 37° C. for 5 min, while shaking at 200 rpm. Finally, a conversion reaction was performed in the presence of 50 mg of Msm-T-HA2 on a 1 L jar scale. At 0, 10, 30, 60, 120, and 180 min during incubation at 37° C., 100 μl, of the enzyme reactions was taken and mixed with 100 μL of 33.2% TCA to stop the enzymatic reaction. The samples taken were diluted in 0.1 N HCl and analyzed for cysteine and cystine contents using LC. Also, the Gaitonde method was used to determine the amount of cysteine. Concentrations of the substrates and the enzyme used in the conversion reaction process are summarized in Table 18, below. The amount of the substrates used is represented by a unit of mL.

TABLE 18

| | pH 9.01 after addition of $Na_2S$, pH 9.16 after filtration | | |
|---|---|---|---|
| OPS Fermentation Broth | Final | | volume |
| Final OPS concentration | 101.47 | mM | |
| Msm-T-HA2 (2.59 μg/μL) | 50 | μg | 19 |
| $Na_2S$ (72 g) | 300 | mM | 0 |
| 10 mM PLP | 0.1 | mM | 10 |
| OPS Broth (19.317 g/l) | 104.42 | mM | 1000 |
| D. W | | | 0 |
| Total | | | 1029 |

The concentrations of cysteine in the reaction mixture obtained after the conversion reaction performed under the condition of Table 18 were quantitatively analyzed by the Gaitonde method and LC, and the results are shown in FIG. 6. When 19.317 g/L OPS broth was incubated for 2 hours in the presence of 50 mg of Msm-T-HA2, as seen in FIG. 6, the amount of produced cysteine or cystine peaked to up to 9.075 g/L, indicating that cysteine and cystine can be produced from OPS at a rate of 71.83% by an enzymatic conversion process on 1 L jar scale.

TABLE 19

| | Cysteine/cystine Conversion Rate (%) | | | | | |
|---|---|---|---|---|---|---|
| | Time | | | | | |
| | 0 min | 10 min | 30 min | 60 min | 120 min | 180 min |
| OPS broth | 10.81 | 28.08 | 51.26 | 67.21 | 71.83 | 69.45 |

TABLE 20

| | Cysteine/cystine (g/L) | | | | | |
|---|---|---|---|---|---|---|
| | Time | | | | | |
| | 0 min | 10 min | 30 min | 60 min | 120 min | 180 min |
| OPS broth | 1.366 | 3.548 | 6.476 | 8.492 | 9.075 | 8.775 |

INDUSTRIAL APPLICABILITY

As described hitherto, the OPSS mutants of the present invention can be useful for the mass production of L-cysteine, which and whose derivatives can find applications in a variety of fields including the pharmaceutical industry (for treatment of bronchial diseases), the cosmetics industry (in hair shampoo, compositions for permanent waves, etc.), and the food industry (antioxidants, flavorant enhancers, dough aids, etc.).

The invention claimed is:

1. An isolated *Mycobacterium smegmatis*-derived O-phosphoserine sulfhydrylase (OPSS) mutant, having O-phosphoserine sulfhydrylase activity and the same amino acid sequence as that of SEQ ID NO: 1 except for deletion of the last three to seven C-terminal amino acids of SEQ ID NO: 1, and (i) substitution of the proline residue (Pro) at position 77 of SEQ ID NO: 1 with a serine residue (Ser), or (ii) substitution of the threonine residue (Thr) at position 131, the lysine residue (Lys) at position 137, and the threonine residue at position 238 of SEQ ID NO: 1 with an alanine residue (Ala), an asparagine residue (Asp), and a serine residue (Ser), respectively.

2. The isolated *Mycobacterium smegmatis*-derived OPSS mutant of claim 1, wherein the last five C-terminal amino acid residues of SEQ ID NO: 1 are deleted.

3. The isolated *Mycobacterium smegmatis*-derived OPSS mutant of claim 1, having the amino acid sequence of SEQ ID NO: 3.

4. The isolated *Mycobacterium smegmatis*-derived OPSS mutant of claim 1, having the amino acid sequence of SEQ ID NO: 4.

5. The isolated *Mycobacterium smegmatis*-derived OPSS mutant of claim 1, showing optimal activity under conditions comprising:

i) presence of PLP (pyridoxal-5'-phosphate) at a concentration of about 0.001 to about 2 mM, or presence of DTT (dithiothreitol) at a concentration of about 0.001 to about 100 mM;

ii) a reaction temperature range of 25 to 60° C.; and iii) a pH range of 6.0 to 10.0.

6. A method for producing cysteine comprising reacting O-phospho-L-serine (OPS) with a sulfide in the presence of the isolated *Mycobacterium smegmatis*-derived OPSS mutant of claim 1.

7. The method of claim 6, wherein the isolated *Mycobacterium smegmatis*-derived OPSS mutant has the amino acid sequence of SEQ ID NO: 3 or 4.

8. The method of claim 6, wherein the isolated *Mycobacterium smegmatis*-derived OPSS mutant shows optimal activity under conditions comprising:

(i) presence of PLP (pyridoxal-5'-phosphate) at a concentration of about 0.001 to about 2 mM, or presence of DTT (dithiothreitol) at a concentration of about 0.001 to about 100 mM;

(ii) a reaction temperature range of 25 to 60° C.; and (iii) a pH range of 6.0 to 10.0.

9. The method for producing cysteine of claim 6, wherein the OPS is in a purified form or in a fermentation culture.

10. The method for producing cysteine of claim 6, wherein the sulfide is selected from the group consisting of $Na_2S$, NaSH, $(NH_4)_2SH$, $H_2S$, and $S_2O_3$, all being in a gas or liquid state.

11. The method for producing cysteine of claim 6, wherein the sulfide is used at a mole concentration which is 0.1 to 3 times higher than the mole concentration of OPS.

* * * * *